US006852698B2

(12) United States Patent
Buhimschi et al.

(10) Patent No.: US 6,852,698 B2
(45) Date of Patent: Feb. 8, 2005

(54) FREE RADICAL SCAVENGERS OR PROMOTERS THEREOF AS THERAPEUTIC ADJUVANTS IN PRETERM PARTURITION

(76) Inventors: Irina A. Buhimschi, 10001 Windstream Dr., #307, Columbia, MD (US) 21044; Carl P. Weiner, 5 Roland Ct., Baltimore, MD (US) 21204

(*) Notice: Subject to any disclaimer, the term of this patent is extended or adjusted under 35 U.S.C. 154(b) by 257 days.

(21) Appl. No.: 09/765,476

(22) Filed: Jan. 18, 2001

(65) Prior Publication Data

US 2001/0031731 A1 Oct. 18, 2001

Related U.S. Application Data

(60) Provisional application No. 60/176,575, filed on Jan. 18, 2000.

(51) Int. Cl.[7] .............................................. A61K 38/44
(52) U.S. Cl. ...................................................... 514/18
(58) Field of Search ................................ 514/18, 28, 2, 514/8, 562, 423, 645; 424/94.4; 530/307, 350

(56) References Cited

U.S. PATENT DOCUMENTS

| 5,508,045 A | 4/1996 | Harrison et al. |
| 5,648,393 A | 7/1997 | Stamler et al. ............. 514/562 |
| 5,910,482 A * | 6/1999 | Yallampalli et al. .......... 514/12 |

FOREIGN PATENT DOCUMENTS

| EP | 60197669 | 7/1985 | |
| JP | 60197669 A | 10/1985 | ......... C07D/311/72 |
| JP | 08325153 | 10/1996 | |
| WO | 9312068 A | 10/1993 | |

OTHER PUBLICATIONS

Coutsoudis et al. Randomized trial testing the effect of vitamin A supplementation on pregnancy outcomes and early mother–to–child HIV–1 transmission in Durban, South Africa. South African Vitamin A Study Group. AIDS. Aug. 20, 1999;13(12):1517–24.

Cherouny et al. The effect of the antioxidant, butylated hydroxy anisole, on peroxide–induced and spontaneous activity of the uterus from the pregnant rat. Biol Reprod. Jul. 1989;41(1):98–103.

(List continued on next page.)

Primary Examiner—Karen Cochrane Carlson
Assistant Examiner—Sheridan K Snedden
(74) Attorney, Agent, or Firm—Jackson Walker LLP

(57) ABSTRACT

The usage of compounds that improve fetal and neonatal outcome of preterm birth is described. These compounds are scavengers of ROS, their precursors, and agents that induce production of the scavengers. Examples of these compounds are glutathione, NAC, antioxidants, and spin trapping compounds. These compounds improve fetal outcome by inhibiting a fetal inflammatory process that may affect the fetus independently of prematurity. This fetal inflammatory response is characterized by increased cytokine and matrix metalloproteases (MMP) levels both in the mother and fetus and may be modulated by ROS at different levels. Targeting ROS formation with compounds such as specific antioxidants, glutathione or spin trapping compounds, their precursors, and/or agents which induce their production will suppress both the direct effects of ROS and its indirect effects through cytokines and MMPs already circulating in the system. This therapeutical intervention would limit the pathophysiologoical chain of events that ultimately leads to PPROM, preterm birth and/or adverse fetal and neonatal outcome.

17 Claims, 9 Drawing Sheets

OTHER PUBLICATIONS

Barrett et al. Potential role of ascorbic acid and beta–carotene in the prevention of preterm rupture of fetal membranes. □□Int J Vitam Nutr Res. 1994;64(3):192–7.

Buhimschi et al. Reduction–Oxidation State (Redox) Regulation of Matrix–Metalloprotease Activity in Human Fetal Membranes.□□Am J Obstet Gynecol. Jan. 1999, Abtract 438: S128.

Lamont RF. The prevention of preterm birth with the use of antibiotics. Eur J Pediatr. 1999 Dec;158 Suppl 1:S2–4. Abstract.

Katz VL, Farmer RM. Controversies in tocolytic therapy. Clin Obstet Gynecol. 1999 Dec;42(4):802–19. Abstract.

Sander CS, Hipler UC, Wóllina U, Elsner P. Inhibitory effect of terbinafine on reactive oxygen species (ROS) generation by Candida albicans. Mycoses. 2002 Jun;45(5–6):152–5.

Goldenberg RL. The management of preterm labor. Obstet Gynecol. 2002 Nov;100(5 Pt 1):1020–37. Review.

Bailou, Veronique, International Search Report with Attachments, May 25, 2001, European Patent Office.

Buhimschi, I.A., et al, Reduction oxidation state (redox) regulation of matrix–metalloprptease activity in human fetal membranes, Jan 1999, p. S128; CA, USA.

Buhimschi, I.A., et al, Glutathione supplementation increases fetal survival after endotoxin administration in a murine model, Jan 2000, p. S44, FL, USA.

Coutsoudis Anna et al, Randomized trial testing the effect of vitamin A supplementation on pregnancy outcomes and early mother–to–child HIV–1 transmission, Aug 1999, p. 1517–1524, South Africa.

Rush D, et al, Longitudinal study of pregnant women, 1988, p. 439–483.

Kuraray, K., Patent Abstract of Japan, vol. 10, No. 056, Mar. 1986.

Yamada Y., Patent Abstract of Japan, vol. , No. 04, Apr. 1997.

Barrett B., Potential role of ascorbic acid and beta carotene in the prevention of preterm rupture of fetal membranes, 1994, pp. 192–197.

Cherouny Ph, et al, The effect of the antioxidant butylated hydroxyanisole on peroxide induced . . . , vol. 41, 1989, pp. 98–103.

Buhimschi, I.A., The nitric oxide pathway in pre–eclampsia, vol. 4, Jan. 1998, pp. 25–42.

Garfield, Robert et al, The role of nitric oxide in preterm labor and pre–eclampsia, vol. 5, 1999, pp. 351–358.

Chwalisz Kristof et al, Role of notric oxide in the uterus and cervix, Journal of Prenatal Medicine, vol. 26 pp. 448–457.

* cited by examiner

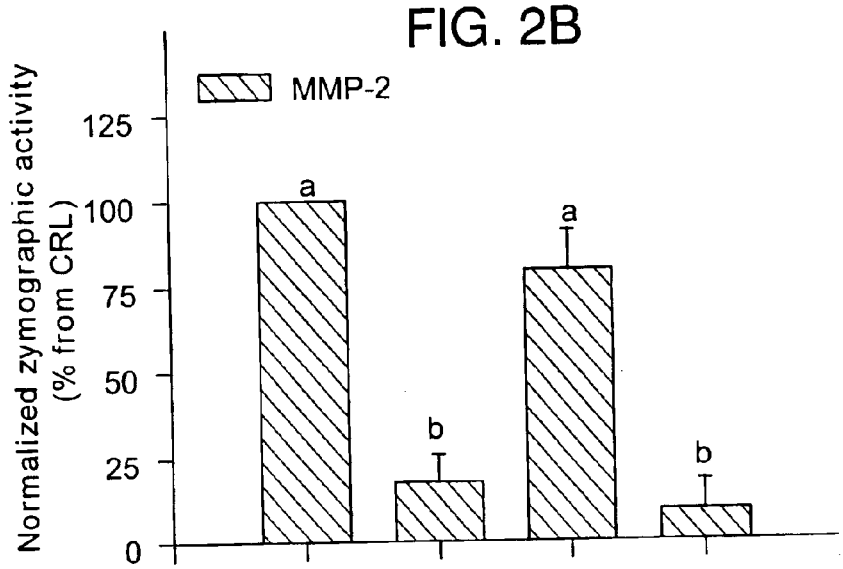
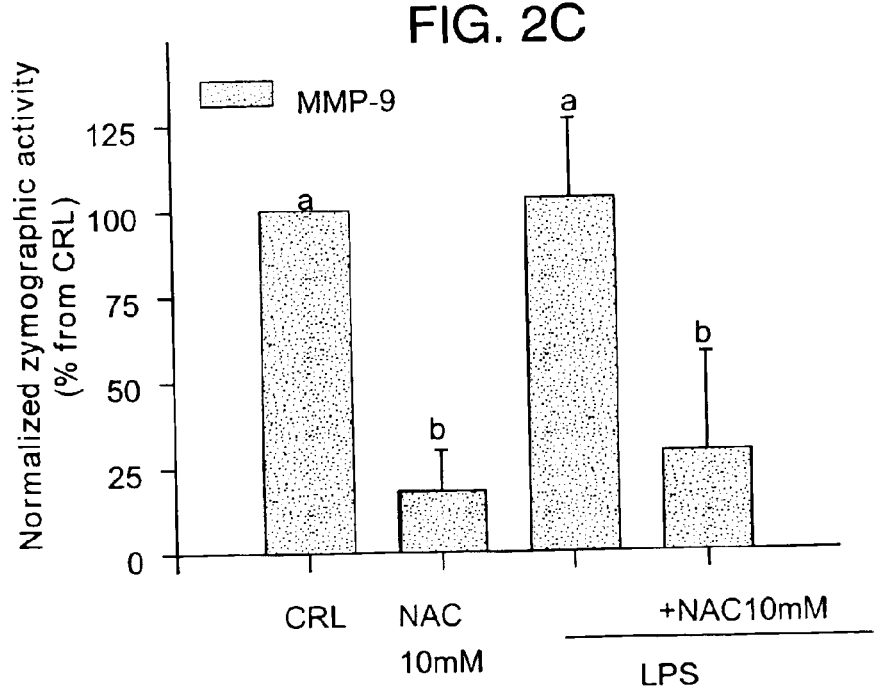

CRL　　　X+XO　　　X+XO+SOD

LPS　　　NAC　　　LPS+NAC

X+XO

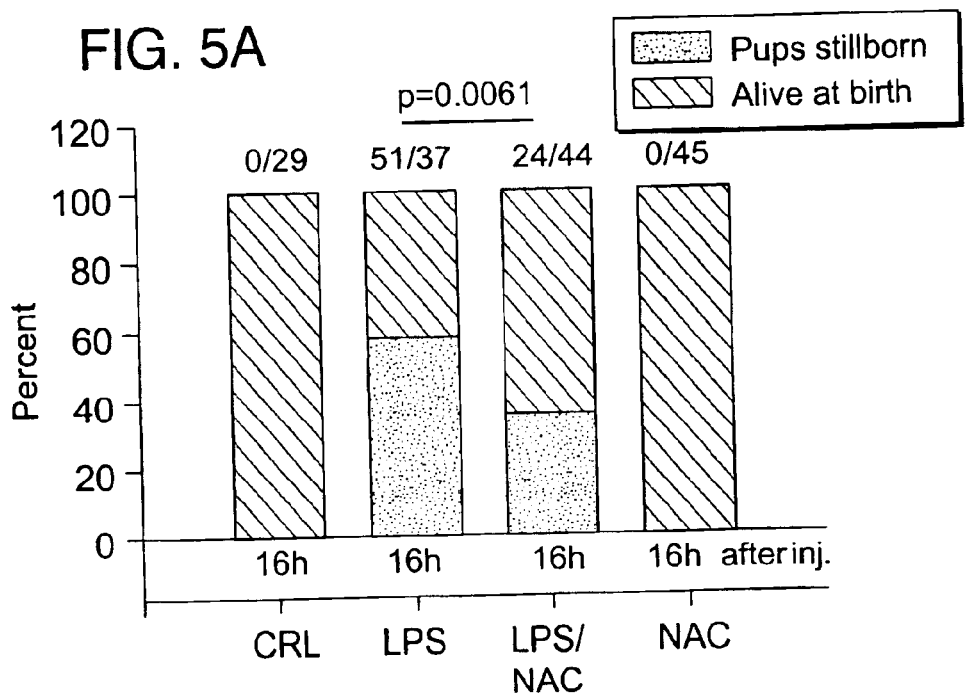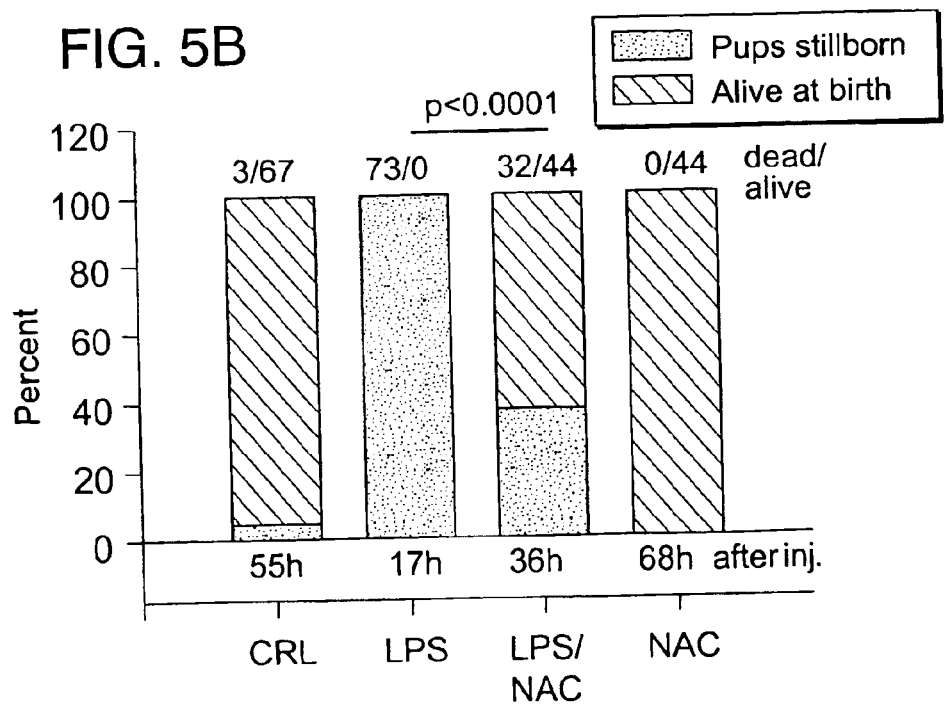

FREE RADICAL SCAVENGERS OR PROMOTERS THEREOF AS THERAPEUTIC ADJUVANTS IN PRETERM PARTURITION

CROSS-REFERENCE TO RELATED APPLICATIONS

Priority is claimed from provisional application U.S. Ser. No. 60/176,575 filed on Jan. 18, 2000, and incorporated by reference herein.

BACKGROUND

1. Field of Invention

This invention relates to therapeutic compounds that improve the outcome of preterm deliveries. More specifically, this invention relates to the usage of compounds that are free radical scavengers or that promote the production of free radical scavengers to prevent adverse fetal outcomes in conditions with high free radical production, preterm deliveries or premature rupture of membranes or even inhibit preterm deliveries.

2. Description of Related Art

Clinical Context

Preterm birth is the major cause of perinatal morbidity and mortality in the world.

Prematurity is responsible for 75% of infant mortality and 50% of long-term neurological handicaps, including blindness, deafness, developmental delay, cerebral palsy, and chronic lung disease (Berkovitz and Papiemik, 1993; Creasy 1993). Any treatment that alters the events of preterm birth or prevents it could profoundly reduce neonatal mortality and morbidity. Even a relatively brief delay in the timing of delivery can have major benefit. Survival rates improve by some 2% per day from the 23rd to the 26th week of pregnancy (i.e. from 16% at 23 weeks to 57% at 26 weeks) reaching 80% at 28 weeks and over 90% by 30 weeks of gestation (Haywood et al., 1994). Yet, there are no agents that prolong pregnancy complicated by preterm labor by more than 48 hours compared to placebo. The health care costs from prematurity are enormous. It is estimated that the total cost per survivor with a birthweight of less than or equal to 900 g (approximately 27 of 40 weeks) in the U.S. exceeds his or her's total average life-time earnings. Over 4 billion dollars (35% of health care costs for all infants) is spent for the care of low-birth-weight infants (Iams, 1995).

The cause of most preterm births is unknown (Bernstein et al., 1998). Current evidence suggests the etiology is multifactorial with a fetal inflammatory syndrome contributing to a large proportion. Both intrauterine (chorioamnionitis) and systemic infections are proposed as important causes of preterm labor (Romero et al., 1990). Systemic maternal infections such as pyelonephritis, pneumonia, syphilis and malaria, for example, are all associated with preterm labor and preterm birth (Gibbs et al., 1992). Colonization of the lower genital tract with a variety of microorganisms may lead to ascending intrauterine infection that in turn results in preterm labor. Microbial invasion of the amniotic cavity occurs in 10% of the patients with preterm labor and intact membranes (Romero et al., 1990) and in 38% of the patients with preterm premature rupture of membranes (PPROM) (Romero et al., 1990). Molecular biologic techniques such as PCR, which is more sensitive than culture, detect bacteria in 60% of the pregnancies complicated with preterm labor (Markenson et al., 1997). Infection-related preterm labor likely involves the release of inflammatory cytokines host defense mechanisms in response to bacterial products (i.e. lipopolysaccharide: LPS). It is believed that the pro-inflammatory cytokines (IL-1, TNFα, IL-8 etc.) stimulate the production of uterotonins (agents that cause uterine contractions), such as prostaglandins, leukotrienes and oxytocin, by the decidua and fetal membranes, eventually leading to the onset of labor. The cytokines may also trigger local mechanisms of cervical ripening and maturation of fetal membranes, that requires the recruitment of inflammatory cells, the release of metalloproteinases (MMPs), and finally the degradation of the extracellular matrix, leading to effacement and dilatation of the uterine cervix or to the rupture of fetal membranes (Romero et al., 1988).

Recently, it was suggested that the levels of IL-6, a pro-inflammatory cytokine, in the fetal circulation correlate strongly with poor neonatal outcome (Gomez et al., 1998). This correlation suggests that at least some neonatal complications are not caused by prematurity per se but are the effect of a fetal inflammatory syndrome. In other words, the stimulus for preterm birth may also directly or indirectly adversely affect the fetus probably through maternal or fetal adaptive responses that may become maladaptive (such as excessive inflammation). This hypothesis is supported by the observation that the neonatal mortality rate is increased in the presence of chorioamnionitis when adjusted for gestational age at delivery (Seo et al., 1992). Furthermore, neonatal morbidity is also significantly increased in the presence of chorioamnionitis. An increased number of inflammatory cells are described in the lungs of infants born to mothers with chorioamnionitis and the resulting pneumonitis lesion is considered a contributor to the increased chronic lung diseases so highly prevalent in these infants (Grigg et al., 1993; Waterberg et al., 1996). Even long-term handicaps such as cerebral palsy are significantly associated with intrauterine infection when controlled for gestational age (Murphy et al., 1995).

Ultrasonographically detectable neonatal brain white matter lesions are the most important prospectively identifiable risk factor for cerebral palsy, defined as sustained neurologic disability with aberrant control of movement and posture appearing early in life. The presence of these lesions are significantly correlated with the level of inflammatory cytokines in amniotic fluid (Yoon et al., 1997a) and in the brain at post-mortem, the periventricular leukomalacia lesions where examined immunohistochemically for the presence of IL-1β, IL-6 and TNFα (Yoon et al., 1997b). However, antagonists of IL-1β or TNFα where not sufficient in preventing either preterm birth or fetal lethality in an endotoxin-injected mouse model suggesting that these cytokines may be only an associated marker of the mounted inflammatory response (Fidel et al., 1997).

Pathophysiological Significance of the Oxidant/Antioxidant Balance

Oxygen ($O_2$) is paramagnetic in the ground state and contains two unpaired electrons whose spins are parallel. This results in a spin restriction that hinders the insertion of pairs of electrons and favors a univalent reduction (Taube, 1965). The univalent reduction of dioxygen to water involves the formation of partially reduced intermediates, (reactive oxygen species; ROS) such as superoxide radical-anion ($O_2 \cdot^-$), hydrogen peroxide ($H_2O_2$), and the hydroxyl radical ($OH \cdot$). These partially reduced intermediates are very reactive and are the cause of oxygen toxicity and mutagenicity (Moody et al., 1982). Most living organisms have evolved well-integrated antioxidant defense mechanisms (scavengers) that include superoxide dismutases (SOD), catalase, glutathione peroxidases, reduced glutathione (GSH), β-carotene, and vitamins C (ascorbic acid) and E.

Under normal respiration, a small but significant amount (1–5%) of the total oxygen consumed is reduced via the univalent pathway. Thus, ROS are normal products of the biological reduction of oxygen and their steady-state concentration is kept low by the above noted scavengers. There could be, however, another evolutionary reason for ROS formation: signal transduction (Storz et al., 1990). Most sources of ROS involved in signal transduction seem to initially generate $O_2.^-$, with hydrogen peroxide ($H_2O_2$) being formed as a result of dismutation of $O_2.^-$.

a) Modulation of Cytokine Production

Several lines of evidence demonstrate that the inflammatory response (as reflected in the cytokine levels) to bacteria or bacterial products (e.g. LPS) is dependent on the oxidant/antioxidant balance. An increase in pro-oxidants or a decrease in antioxidants would alter the redox balance with similar cellular outcomes. The involvement of oxidants in cytokine production is suggested by a study where $H_2O_2$ stimulated IL-8 release dose-dependently in human whole blood (DeForge et al., 1992). Significantly, oxidant scavengers inhibited the LPS-stimulated release of IL-8 (DeForge et al., 1992). The production of TNFα is also regulated by redox-dependent mechanisms since treatment of endotoxemic mice and dogs with the antioxidant N-acetylcysteine (NAC) reduces TNFα activity (Peristeris et al., 1992; Zang et al., 1994). Conversely, glutathione depletion with buthinone sulphoximine (BSO, an inhibitor of glutathione synthesis) exacerbates ROS induced-cell injury (Yang et al., 1995; Wakulich and Tepperman, 1997). This effect is not limited to glutathione-modulating agents because spin traps (which are chemical compounds that directly "trap" and thereby inactivate different classes of ROS) significantly reduce mortality when administered in a murine endotoxic shock model 30 minutes before and 120 minutes after endotoxin (French et al., 1994).

b) Implications of ROS/NO Interaction for Preterm Birth

Another possibility for ROS to act as signal transducers is indirectly by modifying the bioavailability of another free radical, nitric oxide (NO) (Gryglewski et al, 1986). NO is an endogenously synthesized free radical produced by a variety of mammalian cells including neurons, smooth muscle cells, macrophages, neutrophils, platelets and others (reviewed by Nathan, 1992). Several groups report that a NO-cyclic guanosine monophosphate (cGMP) pathway exists in the rat (Yallampalli et al, 1992), rabbit (Sladek et al., 1993), guinea pig (Weiner et al., 1994) and human myometrium (Buhimschi et al., 1995). In all these species, the NO system is upregulated during pregnancy in either the myometrium or placenta (Yallampalli et al, 1992; Sladek et al.; 1993; Weiner et al., 1994; Buhimschi et al., 1995). This suggests to some that NO generation during gestation may contribute to the maintenance of uterine quiescence during pregnancy while its withdrawal prior to term may trigger parturition. A reversal of this scenario occurs in the cervix where the high NO output and inducible NO synthase expression occurs during rat labor suggesting a role for NO in the process of collagenolysis associated with cervical ripening (Buhimschi et al., 1996).

Several missing links emerge from the above sequence of events. How can increased NO produced in the uterus have such a dramatically different effect than NO produced in the cervix? Why do endotoxin-injected animals deliver prematurely despite a high nitric oxide production? (Buhimschi et al., 1996). One possible explanation is that the action of NO is modified by the oxidant/antioxidant balance as the coinciding spatial and temporal formation of high superoxide ($O_2.^-$) and NO amounts results in peroxynitrite (Huie et al., 1993), a powerful long-acting non-radical oxidant that oxidizes a number of biomolecules, including membrane phospholipids, sulfides, thiols, deoxyribose, as well as ascorbate and inhibits mitochondrial electron transport (Beckman and Crow, 1993). Peroxynitrite can also nitrate free or protein-associated tyrosine to generate nitrotyrosine (Ischiropoulos et al., 1992), which is considered as a marker for peroxynitrite action. The rate constant for the reaction generating peroxynitrite (i.e. the probability for the reaction to occur) is higher in systems that produce both NO and $O_2.^-$ than those for the reactions between $O_2.^-$ and SOD or NO and heme compounds (one of the clearance mechanisms of NO) (Pryor and Sqadrito, 1995). The possibility that under certain conditions the interaction between NO and ROS changes the effect of the free radical alone might explain the difference in the effects of a high NO output in the uterus (physiologically generated by non-inflammatory uterine cells during gestation) versus a high output of NO in the cervix (physiologically generated by inflammatory cells during ripening). Cervical softening may therefore be an example of a physiological spatially contained inflammatory reaction resulting in collagenolysis and tissue remodeling. It is well known that during the process of cervical softening the cervix becomes infiltrated with polymorphonuclear leukocytes (Junquiera et al., 1980). However, inflammatory cells produce large amounts of ROS (McCord et al., 1980) and of NO (MacMicking et al., 1997) and therefore peroxynitrite "provisionally". In contrast the NO generating cells from the uterus during pregnancy produce only minimal $O_2.^-$ and mostly by the endogenous xanthine oxidase activity (Telfer et al., 1997). In intrauterine infection or chorioamnionitis, an NO-ROS interaction can also occur in the uterus and by analogy, divert NO from its physiological role towards peroxynitrite, that in turn may contribute to the spread of a process ending in preterm delivery and poor fetal outcome.

c) Modulation of Matrix-Metalloprotease Activity by ROS

Matrix metalloproteases are a family of endopeptidases that collectively cleave most if not all the constituents of the extracellular matrix. Major members of this family are interstitial collagenase (MMP-1), 72-kDa type IV collagenase (MMP-2, 72-kDa gelatinase), stromelysin (MMP-3) and 92-kDa type IV collagenase (MMP-9, 92-kDa gelatinase). These enzymes are secreted into the intercellular compartment as proMMPs and require an activating agent to cleave apropeptide sequence and/or perturb their conformation. Autocatalytic processes, with further propeptide sequence cleavage, result in the fully active enzyme (reviewed by Brikedal Hansen et al., 1993).

Several MMPs (MMP-1, MMP-2, MMP-3, and MMP-9) are expressed in fetal membranes (Fortunato et al., 1997; Parry and Strauss, 1998). Increased MMP-9 activity in amniotic fluid (Athayde et al., 1998), human fetal membranes (Fortunato et al., 1997) and human plasma (Osmers et al., 1994) is reported during spontaneous labor at term. However, recent data suggest that preterm labor and preterm premature rupture of membranes are both associated with further elevated activity of MMP-9 in amniotic fluid (Athayde et al., 1998) and anmio-chorionic membranes (Fortunato et al, 1997). Modulation of matrix-metalloprotease activity by ROS may be relevant for preterm births that present initially with preterm premature rupture of membranes (PPROM). Significantly, these infants have a higher incidence of neonatal mortality and morbidity. In addition, the majority of infants with long term sequelae have documented PPROM before 24 weeks of gestation (Fanarroff et al., 1995).

MMP (particularly MMP-9) activation is a general feature of several inflammatory processes characterized by high cytokine output such as periodontal disease, rheumatoid arthritis and asthmatic airway inflammation (reviewed by Brikedal Hansen et al., 1993). Furthermore, the results of several in vitro experiments in culture conditions reveal a causative relationship between multiple cytokines (IL-1, IL-6, IL-8, TNFα; lipopolysaccharide: LPS) and both MMP-9 expression and activity (Fortunato et al., 1997; Esteve at al., 1998; Gottschall et al., 1995). In addition, modulation of the reduction/oxidation state of the environment alters MMP activity directly as well as the magnitude of the response induced by cytokines. Specifically, an increase in pro-oxidants or a decrease in antioxidants (i.e., altering the redox balance) increases MMP activity. Human heart fibroblasts are redox sensitive and under oxidative conditions are activated to concurrently express metalloproteases and TIMPs (Tyagi et al., 1996). Further, thiol (reduced glutathione and NAC) but not non-thiol reducing agents inhibit MMP activation and increase tissue inhibitors of MMPs expression in transformed cells. Incubation of cultured human vascular smooth muscle cells with a superoxide-generating mixture increases the amount of active MMPs, while NO donors have no noticeable effect (Rajagopalan et al., 1996). In cultured cartilage, antioxidants such as N-acetyl cysteine (NAC) and glutathione inhibit the chondrolytic activity of fibronectin fragments (Homandberg et al., 1996) that act through catabolic cytokine action mediated by IL-1, IL-6 and TNFα (Rathakrishnan et al., 1992). Endotoxin (LPS) activates MMP-9 in cultured microglia (Gottschall et al., 1995) and MMP-2 in cultured rat mesangial cells (Trachtman et al., 1996) and both IL-1 and TNFα reportedly operate at least partially through ROS (Rathakrishnan et al., 1992; Tiku et al., 1990), It has also been shown that the fetal inflammatory response syndrome noted above is characterized by an outpouring of extracellular MMP-9 into the fetal circulation (Romero et al., 1998). High levels of MMP-9 are also found in the cerebral spinal fluid of patients with neurologic spastic diseases (Valenzuela et al., 1999) suggesting that MMP-9 may be a pathogenetical cause in the neural tissue remodeling described in infants with cerebral palsy.

Because of the known association between infection and preterm labor antibiotics are now proposed both as prophylaxis and treatment of preterm labor and delivery (Gibbs et al., 1997). Yet, antibiotics only prevent the release of new cytokines in addition to the microbial cytokine outpouring that occurs from microorganism killing. Said differently, antibiotics alone cannot reduce or inhibit the inflammatory process already underway.

Tocolytic drugs, which presently are the standard tool for the treatment of preterm labor despite their demonstrated inability to delay labor more than 48 hours (Higby et al., 1993), could actually have unintended adverse effects by prolonging the fetal exposure to an unfavorable environment and increase the probability of irreversible tissue damage and subsequently increased mortality or morbidity later in life.

Despite all the afore noted knowledge, no compounds have been put forth as therapeutic agents that address inflammation as a cause of preterm birth the fetal inflammatory process, PPROM, and adverse fetal outcomes.

d) Oxidative Stress: A Converging Point for Factors Causing Preterm Labor and Fetal Morbidity.

There are conditions other than infection and inflammation that stimulate oxidative stress during pregnancy. Cocaine, smoking and alcohol consumption are each well known for this property, although the nature of, and the biochemical pathways by which free radicals are generated in vivo differ. We believe that therapeutic agents as NAC or other antioxidants and ROS scavengers are beneficial in such instances.

Cocaine use is associated with intrauterine growth restriction, stillbirth, placental abruption and congenital malformations (limb reductions). The incidence of preterm labor ranges in cocaine users from 20 to 50% (Little et al., 1989; Feldman et al., 1992). The placental abruptions and cerebral infarcts found in neonates exposed to cocaine in utero are attributed to the vasoactive effect of cocaine, which inhibits the uptake of catecholamines and serotonin by nerve endings. The net result is vasoconstriction and an ischemic-reperfusion injury. (Chasnoff et al., 1985). Animal studies confirm that the teratogenic effect of cocaine is secondary to vasoconstriction and local hemorrhage. (Webster and Brown-Woodman, 1990). In addition, cocaine increases the placental thromboxane to prostacyclin ratio. (Monga et al., 1994). As noted previously, the first oxygen free radical generated by an ischemic-reperfusion injury is $O_2^-$ produced via the activation of xanthine oxidase in the oxygen-deprived tissue. This is followed by mitochondrial leakage and lastly inflammatory cell recruitment in the area of necrosis. Alternatively, cocaine produces excess free radical metabolites during its metabolism in the hepatic microsomes, a possibility that could explain the hepatotoxicity of cocaine (Boelsteri et al., 1992). Cocaine also affects the fetus through maternal injury since vascular disruptions and free radical injury does not occur in embryos co-cultured with cocaine, and the maternal administration of a specific antioxidant inhibits lipid peroxidation by cocaine (Zimmerman et al., 1994). Rat fetuses exposed to cocaine display accelerated lung maturation unparalleled by an induction of antioxidant enzymes (Sosenko, 1993). These studies suggest that cocaine use results in oxidative stress with profound fetal consequences. In addition to the genesis of oxidative stress, acute cocaine exposure increases myometrial contractile activity (Monga et al., 1993a; Monga et al 1993b) by increasing intracellular calcium (Formin et al., 1999) yet another mechanism that may contribute to preterm delivery.

Ethanol consumption during pregnancy is associated with preterm labor in addition to its well-publicized fetotoxic effects. The fetal toxicity of ethanol is polymorphic. The described fetal alcohol syndrome includes pre- and postnatal growth disturbance, mental retardation, heart defects, limb defects and a characteristic facial anomaly. (Jones et al., 1973). It is the most commonly identified cause of mental retardation. A significantly increased risk of white matter brain damage is also reported (Holzman, 1995). The underlying mechanism remains largely unknown. In susceptible strains of inbred mice, ethanol produces preterm labor by initiating a cascade of events similar to endotoxin (Salo et al., 1996; Cook et al., 2000). The biochemical alterations induced by ethanol include delayed cell replication, altered membrane fluidity and transport mechanisms that have been linked to oxidative stress-induced membrane damage (Henderson et al., 1999; Kourie, 1998).

There is abundant literature on ethanol-induced free radical formation. These studies confirm that hepatic macrophage NADPH oxidase is the primordial source of $O_2^-$ radicals and $H_2O_2$, and that their levels can be reduced by antioxidant treatment (Nanasumrit et al., 2000). These reactive oxygen intermediates subsequently lead to the formation of 1-hydroxyethyl radicals. Knockout mice lacking NADPH oxidase are resistant to ethanol-induced 1-hydroxyethyl radicals formation and hepatic injury (Kono et al., 2000).

Cigarette smoking during pregnancy is another risk factor for preterm delivery. A recent meta-analysis restricted to prospective studies revealed a 1.27 pooled odds ratio (95% confidence interval, 1.21–1.33) with a dose response relationship at low to moderate levels of smoking (Shah and Bracken, 2000). Another recent study suggested that multiparous women have an even higher risk (Kolas et al., 2000).

One of the mechanisms by which smoking induces DNA damage and lung cancer is via HO. radical-mediated mutagenesis (Pourcelot et al., 1999). Of particular interest is the observation that hypoxia produced by smoking triggers the up-regulation of a circulating antioxidant (reduced glutathione) and vasodilator mechanisms. For example, chronic and acute smoking results in a high production of cyclic guanosine monophosphate (cGMP: a vasodilating second messenger of NO) in both urine (Markovitz et al., 1997) and plasma (Dupuy et al., 1995). The level of reduced glutathione in erythrocytes is 35% higher in pregnant women who smoked compared to non-smokers (Laskowska-Klita et al., 1999). Although maternal smoking is associated with higher risk of preterm delivery and a net detrimental effect on pregnancy outcome, these compensatory mechanisms may contribute to the observation that smokers have a lower risk of preeclampsia (Zhang et al., 1999) a disorder where vasoconstriction, hypoxia and possibly decreased endothelial cGMP production are part of the pathophysiologic process.

Sickle cell anemia, thalassemia and glucose-6-phosphate-dehydrogenase deficiency are all hereditary anemic disorders with higher potential for oxidative damage due to chronic redox imbalance in red cells (lower reduced GSH) that often results in clinical manifestation of mild to serve hemolysis in patients with these disorders (Chan et al., 1999). Women with these hereditary anemic disorders have a higher risk of preterm delivery and poor neonatal outcome (Seoud et al., 1994). It has been observed that NAC has the ability to cause a significant diminishment of sickle cell formation in vitro while other antioxidants had no effect (Xunda et al., 1998; Shartava et al., 1999).

Preeclampsia, a syndrome unique to primates and defined by the triad of hypertension, proteinuria and pathological edema during pregnancy had been associated with oxidative stress affecting maternal endothelium. In support of this conclusion, a recent, randomized trial of women at risk for preeclampsia concluded that supplementation with vitamins E and C was effective in preventing occurrence of early markers or symptoms of preeclampsia. The present inventors propose that NAC alone or in combination with other antioxidants to will increase the therapeutic efficacy in preeclampsia.

The present inventors and others have previously reported the chronic competitive inhibition of NO synthesis with L-arginine analogues (NG-ritro-L-arginine methyl ester: L-NAME) can cause hypertension, proteinuria and fetal growth restriction in rats without affecting gestational length if pregnant (Baylis et al., 1992; Yallampalli and Garfield 1993; Molnar et al., 1994). Glomerular damage and histopathological changes in the placental bed similar to human preeclampsia are suggested (Osawa, 1996). The increased blood pressure and fetal growth restriction are reversed by simultaneous infusion of L-arginine but not D-arginine (not a substrate for NOS) (Buhimschi et al., 1995; Liao et al., 1996) The fetuses from L-NAME treated rats frequently exhibit distal limb necrosis (Dicket et al., 1994)/A recent study suggests that chronic NO inhibition promotes a state of oxidative stress with HO-mediated DNA damage (Tsukahara et al., 2000). Recent findings from our group reveal that some colonies of rats are refractory to NO inhibition and the symptoms of preeclampsia do not occur despite continuous L-NAME infusion throughout pregnancy (Buhimschi et al., in press). This strongly suggests that the extent of clinical manifestations in preeclampsia may reflect the interaction of a multitude of antioxidant and vasodilatory mechanisms that can compensate for one another to some extent.

SUMMARY OF THE INVENTION

It is a goal of this invention to prevent ROS formation by administering compounds to pregnant women and/or their fetuses either at great risk of or in preterm labor. It is a goal of this invention that preterm birth be inhibited by preventing ROS formation either alone or in combination with tocolytics and/or antibiotics. It is a further goal of this invention that by preventing the formation of ROS, the outcome of preterm deliveries that do occur and the outcome of fetuses that progressed to term will improve. By prevention of ROS formation is meant either the literal inhibition of ROS formation or the efficient removal of any ROS found.

It is also a goal of this invention to use compounds that prevent or inhibit ROS formation. It is another goal of this invention to administer compounds that prevent or inhibit ROS formation. It is another goal of this invention to use the ROS-inhibiting compounds to stop the subsequent adverse effects of cytokines and MMPs, an indirect affect of ROS.

It is another goal of this invention to administer glutathione to prevent ROS formation. It is a further goal to administer glutathione precursors to inhibit ROS formation. It is a further goal to administer agents that stimulate the production of glutathione to prevent ROS formation.

It is another goal of this invention to administer anti-oxidants to prevent ROS formation. It is a further goal to administer anti-oxidant precursors to inhibit ROS formation or concentration enhancement. It is a further goal to administer agents that stimulate the production of anti-oxidants to prevent ROS formation.

It is another goal of this invention to administer spin trapping compounds to prevent ROS formation. It is a further goal to administer spin trapping compound precursors to inhibit ROS formation.

It is a further goal to administer agents which stimulate the production of spin trapping compounds to prevent ROS formation.

It is a goal of this invention to prevent PPROM by the administration of compounds that prevent or inhibit ROS formation. It is a further goal to administer anti-oxidants, glutathione, glutathione precursors, and/or spin trapping compounds, to prevent PPROM. It is a further goal to administer anti-oxidants, glutathione, glutathione precursors, and/or spin trapping compounds, in combination with tocolytics and/or antibiotics, to prevent PPROM.

It is a goal of this invention to prevent preterm birth by the administration of compounds that prevent or inhibit ROS formation. It is a further goal to administer anti-oxidants, glutathione, glutathione precursors, and/or spin trapping compounds, to prevent preterm birth. It is a further goal to administer anti-oxidants, glutathione, glutathione precursors, and/or spin trapping compounds, in combination with tocolytics and/or antibiotics, to prevent preterm birth.

It is a goal of this invention to prevent adverse fetal outcomes by the administration of compounds that prevent or inhibit ROS formation or concentration buildup. It is a further goal to administer anti-oxidants, glutathione, glutathione precursors, and/or spin trapping compounds, to prevent adverse fetal outcomes. It is a further goal to administer anti-oxidants, glutathione, glutathione precursors, and/or spin trapping compounds, in combination with tocolytics and/or antibiotics, to prevent adverse fetal outcomes.

It is a goal of this invention to prevent adverse outcomes of preterm deliveries by the inhibiting the affects of cytokines and MMPs. It is a goal of this invention to prevent adverse outcomes of PPROM by the inhibiting the affects of cytokines and MMPs.

It is a goal of this invention to prevent adverse fetal, neonatal and or maternal outcomes by the administration of compounds that prevent or inhibit ROS. The adverse fetal outcome may be the consequence of maternal drug (cocaine or ethanol) exposure, smoking asphyxia, hemolytic anemia, sepsis and other conditions associated with increased ROS production in the mother or fetus.

It is a goal of this invention to administer NAC or glutathione, glutathione precursors, and/or spin trapping compounds to women with preeclampsia. It is a goal of this invention to administer NAC or glutathione, glutathione precursors, and/or spin trapping compounds to women with preeclampsia in combination with other antioxidants.

An important aspect of the present invention is an improved therapy to prevent premature labor or to improve the outcome of premature labor in a pregnant animal. This therapy comprises the administration of a free radical scavenger or precursor thereto in an effective amount to a pregnant animal. In some cases, the material may be given directly to a fetus to ensure proper development at that point. This improved therapy may also include the administration of an antibacterial agent, a tocolytic agent or other agent commonly used to help assure a patient's health. In some cases, an agent may be used in the therapy of the present invention that induces the production of endogenous free radical scavengers to a pregnant animal. Commonly induced free radical scavenger would be glutathione. N-acetylcysteine (NAC) are preferred free radical scavengers, the latter being the most particularly preferred. It is understood that the free radical scavenger of the present invention is an antioxidant. Such free radical scavengers can be the commonly used spin trapping compounds.

Thus, the present invention involves preventing premature labor, as well as, preventing the premature rupture of membranes in a pregnant animal. Both of these involve administration of or induction of a free radical scavenger in an animal. The procedures for preventing premature membrane rupture in a pregnant animal are analogous to those preventing premature labor. The route of addition of the free radical scavenger may vary. In particular cases where the fetus is being treated in may be intraamniotic. Effective amounts of the agent of the present invention are those amounts that in fact decrease ambient reactive oxygen species and in some cases nitric oxide as well. In certain cases, reactive oxygen species and nitric oxide interact to have professionally an actual negative effects on membranes and other components of an animal. In addition to free radical scavengers glutathione, and NAC, beta carotene, vitamin C and vitamin E are effective as well. In some cases, an agent may be used that is a precursor of a free radical scavenger, but is in fact a spin trapping compound itself. In certain cases, endogenous inhibitors of ROS can be superoxide dismutase, catalase, glutathione peroxidase. The induction of these enzymes can be beneficial. As far as improving the outcome of preterm deliveries, the pregnant animal or the fetus of that pregnant animal may be treated with the free radical scavengers of the present invention. Although humans are the primary subject of the present invention, it is understood that in certain cases various animals such as monkeys, cows, sheep, chickens, horses, dogs, cats and elephants may also be subjected to this improved therapy. While in most instances the animal being treated, according to the present invention, be a mammal, it is conceivable that certain reptiles and amphibians may be conceivably involved. In an important aspect, the animal being subjected to the therapy of the present invention is a high risk patient selected, for example, from the group consisting of patients with a history of preterm labor, patients with preterm labor, cocaine users, preeclamptic patients and patients with PPROM. In the method and therapy of the present invention, an effective amount of the reactive oxygen scavenger is an amount lessening significantly the level of reactive oxygen species in the patient, particularly at crucial or selected sites in the patient. This amount may vary, but in the case of NAC may be, judging from other regimens that have been used, 600 mg twice daily which may be consumed as a liquid mixture. It may be intravenously administered as a 10% NAC solution in common intravenous vehicles. This may include 3% procysteine administered at 0.4 mmol/kg of bodyweight. Direct administration to the fetus itself may be through the amniotic fluid or even through the umbilical cord.

BRIEF DESCRIPTION OF THE DRAWINGS

FIG. 2B is a graph showing the quantification of amniochorionic MMP-2 (hashed bars) from 5 different patients.

FIG. 2C is a graph showing the quantification of amniochorionic MMP9 (stippled bars) activity from 5 different patients. Data is normalized against the dry weight of the tissue incubated, presented as percent from CRL (mean+SEM) and analyzed by one-way ANOVA with multiple post-hoc Tukey tests. For each graph of FIGS. 2B and 2C, the means with different superscripts are different at a value of $p>0.05$.

FIG. 5A is a graph showing the fetal viability from C57B16 mice after hysterotomy at 16 h after LPS or saline injection.

FIG. 5B is a graph showing the fetal viability from C57B16 mice immediately after the pup was expelled from the vagina. The stippled part of the bars represents the percent of dead pups. The hashed part of the bar represents the percent pups alive at examination. The fraction on the top of the bars depicts the total number of dead/number of fetuses alive counted in a group. The number of mothers analyzed were: n=12 (CRL), n=13 (LPS), n=8 (NAC) and n=12 (LPS/NAC).

DETAILED DESCRIPTION OF THE INVENTION

Figure 1A:
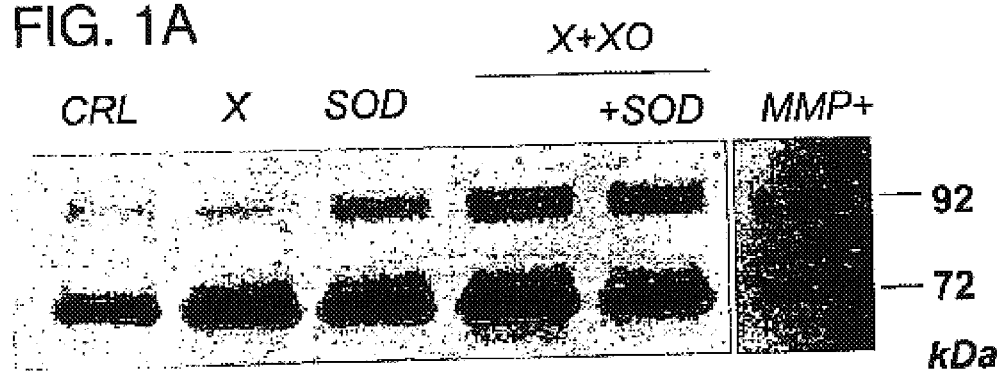
FIG. 1A illustrates a representative inverted substrate gel electrophoresis (gelatin zymography) obtained with medium from human full thickness fetal membranes from patients that delivered at term via an elective C-section were incubated in phosphate buffered saline alone (CRL) or in the presence of xanthine (X: 2 mM), superoxide dismutase (SOD: 500 U/ml), xanthine and xanthine oxidase (X+XO: a source of superoxide-), X+XO+SOD. Recombinant MMP-2 and MMP-9 (MMP+) are run in the right lane. The upper and lower bands correspond to gelatinolytic activities of MMP9 (gelatinase B: 92 kDa) and MMP2 (gelatinase A: 72 kDa), respectively.

Patients likely to benefit from the present invention are identified as either high risk or having an acute problem. High risk patients include but are not limited to: cocaine users, preeclamptic patients, patients with preterm labor, a history of preterm labor, or PPROM. Fetuses with intrauterine growth restriction are likely to benefit. Acute problems include intrapartum hypoxia.

Possible routes of administration for free radical scavengers and other agents of the present invention are: to a mother—include oral, iv, sublingual, inhaled, rectal, vaginal, transmucosal, transcutaneous, intraamniotic, and to the fetus include intraamniotic or via cordocentesis.

Preferred dosages for effective amounts of the agent—oral regimen: In women at risk: 600 mg twice daily (dose used by Tepel et al., New Engl J. Med 2000 for prevention of renal damage). In acute situations the patient will be given a loading dose of 140 mg/kg followed by 70 mg/kg every 3–4 hours (the FDA approved protocol for acetaminophen intoxication). The drug can also be administered as a 5% solution in cola or fruit juice.

a) Effect of ROS Modulation In Vitro on Amniochorionic MMP Activity iv dosage: 10% N-acetyl cysteine in 5% dextrose or other drugs such as 3% Procysteine (L-2-oxothiazolidine-4-carboxylate) administrated at 0.4 mmoles/kg body weight. Drugs are administrated over 30 minutes, every 8 hours (from Bernard et al., Chest 1997—for protective effect against adult respiratory distress syndrome).

Intraamniotic via amniocententesis or amnioinfusion catheter: infused liquid contains 10% buffered N-acetyl cysteine. (no reference just guess. This is an important route of administration to the fetus because the fetus swallows the amniotic fluid so it is equivalent to an oral administration to the fetus.

The drug dosage and bioavailability to the mother and the fetus will indicate therapeutic effectiveness. Kits or assays are envisioned that may measure, for example, NAC (or thiols—not only NAC) in maternal uterine, amniotic fluid, maternal or neonatal blood at delivery or postpartum may have commercial value.

Antioxidant compounds of the present invention include cysteine, glutathione, N-acetylcysteine, L-alpha-acetamido-beta mercaptopropionic acid, S-nitroso-gutathione, N-acetyl-3-mercapto-alanine, butylated hydroxyanisole, butylated hydroxytoluene, L-2-oxothiazolidine-4-carboxylate, vitamin C (ascorbate) and vitamin E (tocopherol). These may be used alone and in combination with each other and/or with desferrioxamine, allopurinol, superoxide dismutase and superoxide dismutase mimetics such as salen-manganese complexes (see U.S. Pat. No. 6,046,188). Spin trapping compounds that can be used as ROS scavengers include nitrones (e.g., phenyl-butyl nitrone, trimethoxyphenyl-butyl nitrone), nitroxides and salicylates.

Spin trapping compounds combined with MRI can be used as a noninvasive method to detect free radical damage to the fetus or maternal reproductive tissues during pregnancy.

Materials and Methods:

Tissues: Full thickness amniochorionic membranes were collected from seven patients without complications of pregnancy undergoing elective C-section at term. The fragment collected was selected from a region at least 10 cm away from the placenta. Immediately after collection, membranes were placed in minimum essential medium (MEM) (Gibco, Grand Island, N.Y.) on ice. Tissue samples were then cut under sterile conditions with a scalpel blade into smaller pieces of similar size. Over the next 30 min., the pieces of membranes were rinsed thoroughly with several changes of MEM and then sterile phosphate buffered saline (PBS) pH=7.8. Preweighed amounts of tissue (approximately 500 mg) consisting of several pieces selected at random were placed in a $CO_2$ incubator with a humidified chamber at 37° C. for 24 hours. Incubations were carried out in a total volume of 2 ml buffer. Both wet weight and dry weight of tissue pieces were determined after incubation and after drying overnight at 60° C., respectively. After incubation the culture-conditioned medium was collected, briefly spun at 1000 g to remove cellular debris and loaded directly on gelatin gels. The concentration of protein in the aliquots of medium was measured with a BCA kit (Pierce, Rockford, Ill.).

Drugs and incubations: Incubations were performed in the presence of xanthine (X: 2 mM), xanthine oxidase (XO: 20 mU/ml), the combination xanthine+xanthine oxidase (X/XO), superoxide dismutase (SOD: 500 U/ml), X/XO/SOD, nitro-L-arginine (a nonspecific nitric oxide synthase inhibitor, LNA: 1 mM), X/XO/LNA, S-nitroso-N-acetyl penicillamine (a nitric oxide donor, SNAP 10 mM), X/XO/SNAP, N-acetyl cysteine (NAC: 0.1, 1, 10 mM), lipopolysaccharide (LPS 100 ng/ml). All chemicals were purchased from Sigma (St. Louis, Mo.) unless otherwise specified.

Extracellular superoxide anion generation: $O_2^-$ was generated enzymatically from the reaction between 2 mM xanthine (X) and 20 mU/ml xanthine oxidase (XO), as described by McCord and Fridovich (1969). Though these amounts are larger than those routinely used for in vitro generation of $O_2^-$ in cell-free experiments, we have based our decision on the presence of both XO and SOD in fetal membranes (Telfer et al., 1997) and on our assumption that the expression of these enzymes will change the efficiency of the X/XO reaction. As a result we monitored the efficiency of the X/XO reaction in our experimental setting by a cytochrome c assay, both in tissue-free conditions as well as in the presence of the tissue (Babior et al., 1973). The reduction of ferri- to ferro-cytochrome c is a process highly selective for extracellular $O_2^-$ and associated with a change in absorbance at 550 nm within 15 min. As proof for the specificity of the reaction, SOD (500 U/ml) completely inhibited the change in absorbance at 550 nm.

Intracellular superoxide anion generation: Pieces of fetal membranes were immersed in Krebs bicarbonate buffer (118 mM NaCl, 4.7 mM KCl, 1.18 MM $MgSO_4$, 1.18 mM $KH_2PO_4$, 11.1 mM D-glucose, 0.016 mM EDTA, 2.2 mM $CaCl_2$, 15.8 mM $NaHCO_3$, pH=7.35–7.4) containing 1 mg/ml nitroblue tetrazolium (NBT), for 180 min. in the $CO_2$ incubator with humidified chamber at 37° C. The soluble yellow form of NBT is reducedby $O_2^-$ generated within the tissue to form an insoluble precipitate of blue-purple formazan. After incubation, the fetal membranes were washed in saline, photographed, placed in 4% formaldehyde and kept overnight in a refrigerator. Specimens were then embedded in OCT Tissue Tek embedding medium (Fisher Scientific, Pittsburgh, Pa.) and frozen in liquid nitrogen. The frozen specimens were cut by cryostat into 20 µm sections, mounted onto electrostatically treated-glass slides (Fisherbrand Superfrost Plus, Fisher Scientific) and counterstained with Neutral Red. They were immediately investigated by light microscopy using a Nikon Eclipse E1000M microscope connected to an MTI DC330 3CCD Color Camera (Dage MTI Inc., Michigan City, Mich.).

SDS-Substrate gel electrophoresis (zymography): For detection of MMPs, equal volumes (15 µl) of conditioned medium (containing the activated MMPs) were mixed in a 1:3 ratio with substrate gel buffer (10% SDS, 4% sucrose, 0.25 M Tris-HCl, pH=6.8 and 0.1% bromphenol blue) and loaded directly onto gels without boiling (Raj agopalan et al., 1996 with modifications). Briefly, type I gelatin was added to a standard Laemmli 10% acrylamide polymerization mixture at a final concentration of 1 mg/ml. Following electrophoresis, the proteins in the gel were renatured by exchanging SDS with Triton X-100 and the gels were incubated overnight at 37° C. in 50 mM TRIS-HCl, pH=7.4 containing 10 mM $CaCl_2$ and 0.05% Brij 35. At the end of the incubation, the gels were stained with 0.5% Coomassie Blue R-250 (Bio-Rad, Hercules, Calif.) in 40% methanol/10% acetic acid, then destained in 40% methanol/10% acetic acid for 1 h. Proteins having gelatinolytic activity appeared as discrete translucent areas of lytic activity on an otherwise blue gel. When the gels are incubated in parallel with 0.01 M EDTA, disappearance of lytic bands confirms the metal dependence of MMP activity. Migration of proteins was compared with that of prestained broad molecular weight markers (Bio-Rad). Further, 10 ng/lane of zymography standards (recombinant MMP-2/MMP-9, Calbiochem, La Jolla, Calif.) were run along with the samples. In order to quantify the gelatinolytic activity of MMPs, the wet gel was scanned on a GS-670 Image Densitometer (Bio-Rad), and analyzed using Multianalyst v1.1 volume quantification system software (Bio-Rad). After image inversion and background subtraction, the amount of lytic activity (which now appears as a black band on a white background) is estimated as optical density over the area of the band ($ODxmm^2$). These values were normalized against the dry weight of the tissue incubated, and further normalized against the value from the lane where the tissue was incubated in PBS alone on the same gel. To evaluate the reliability of the image analysis system, differing amounts of zymography standard (5, 10, 20 ng/lane) were loaded onto one gel and MNP-2 (72 kDa) and MMP-9 (92 kDa) activities quantified separately. The correlation coefficient between MMP concentration as quantified by substrate gel analysis and the amount of protein loaded approached 1. To evaluate the reliability of the normalization, differing amounts of amnio-chorionic tissue (100, 250, 500, 750 mg) were incubated and MMP-2 and MMP-9 activities plotted against the dry weight of the tissue. The correlation coefficient was 0.98.

Statistical analysis: The results are presented as mean +1 SEM of the percent activity from the lane incubated in PBS (CRL) from the same patient and run in the same substrate gel electrophoresis. Multiple comparisons between groups were performed using one-way analysis of variance (ANOVA) followed by multiple post-hoc Tukey tests. A p value <0.05 was considered as the limit for statistical significance.

Results:

MMP levels in human term amnio-chorionic membranes in the absence and presence of REDOX balance modulators: MMP-9 and MMP-2 corresponding to the 92 and 72 kDa lytic bands, respectively, were detected in all tissues, at least after culture conditions (FIG. 1A). In some of the patients, an additional band corresponding to proMMP-9 was observed. There was a large variability in the intensity of the lytic bands among the seven patients justifying the need for the normalization described in the Methods section. $O_2^-$ generated by the X/XO reaction induced a nonsignificant increase in the total amount of protein released in the conditioned medium also justifying the need for a normalization against the dry weight of the tissue rather than against the protein concentration in the medium. The efficiency of the X/XO reaction was confirmed for each experiment by cytochrome c reduction assay.

Figure 2A:
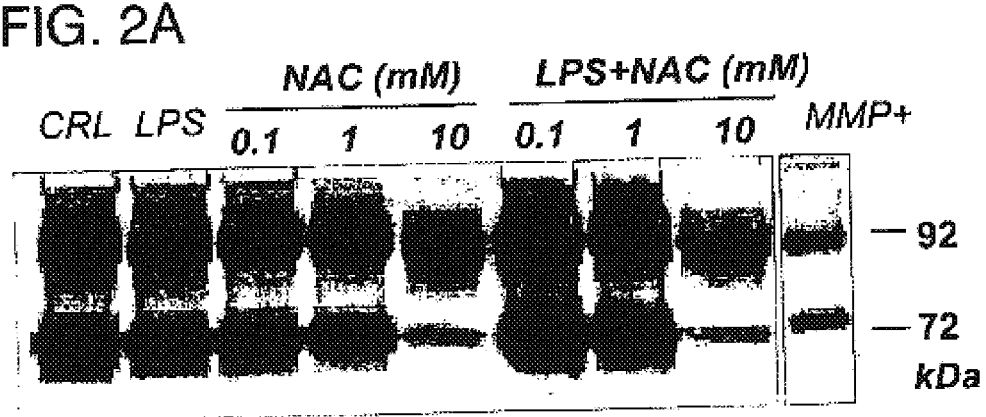
FIG. 2A illustrates inverted substrate gel electrophoresis (gelatin zymography) obtained with the incubation medium from two different patients (A and B) using full thickness fetal membranes from patients that delivered at term via elective an C-section were incubated in phosphate buffered saline alone (CRL) or in the presence of N-acetylcysteine (NAC: 0.1–10 mM), lipopolysaccharide (LPS: 100 nM), LPS+NAC. Recombinant MMP-2 and MMP-9 (MMP+) are run in the right lane. The upper and lower bands correspond to gelatinolytic activities of MMP9 (gelatinase B: 92 kDa) and MMP2 (gelatinase A: 72 kDa), respectively.
Figure 1B:
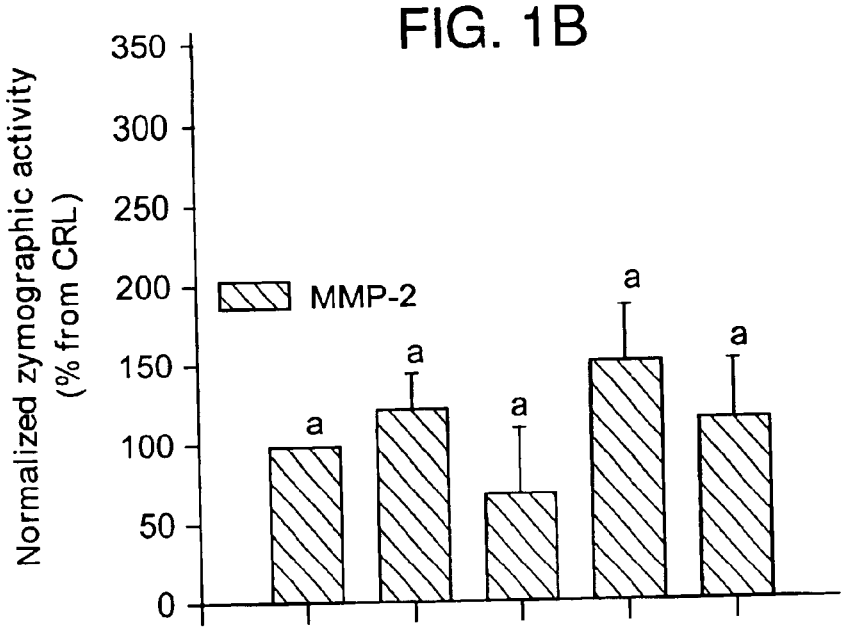
FIG. 1B is a graph showing the quantification of amniochorionic MMP-2 (hashed bars) from 7 different patients.
Figure 1C:
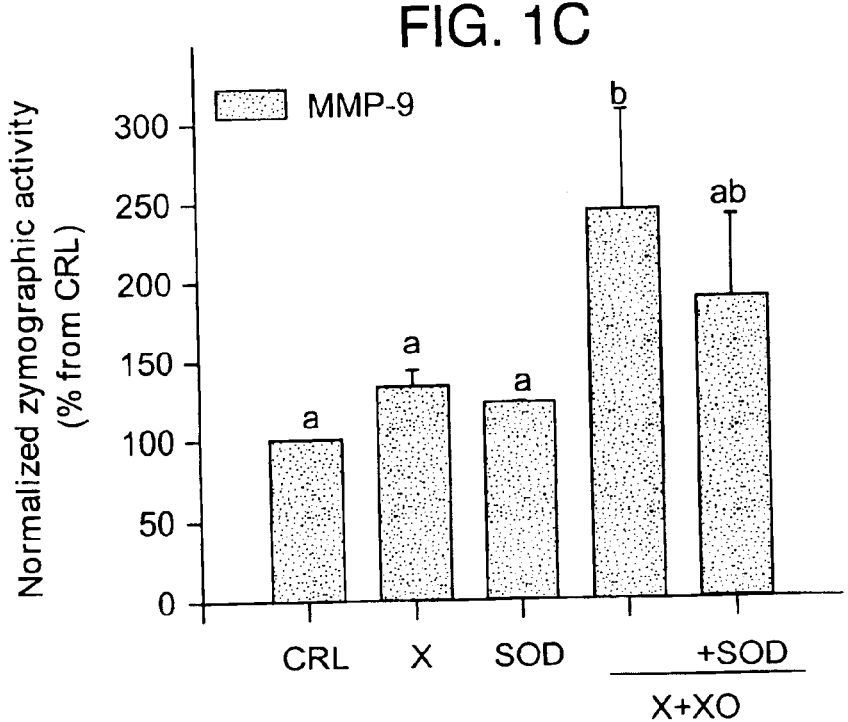
FIG. 1C is a graph showing the quantification of amniochorionic MMP9 (stippled bars) activity from 7 different patients. Data is normalized against the dry weight of the tissue incubated, presented as percent from CRL (mean+ SEM) and analyzed by one-way ANOVA with multiple post-hoc Tukey tests. For each graph of FIGS. 1B and 1C, the means with at least one common superscript are not different at a value of $p>0.05$.

As illustrated in FIG. 11A incubation with X/XO significantly increased MMP-9 concentration. This increase was reversed by simultaneous addition of SOD. A small increase in MMP-9 was observed in some of the patients with xanthine alone probably reflecting endogenous XO activity. Incubation with 10 mMNAC dramatically reduced both MMP-2 and MMP-9 activities to 20% of the levels from the CRL tissue NAC also prevented the increase in MMP-9 induced by X/XO (not shown). Neither NO synthase inhibition, nor the NO donor SNAP had any significant effect on fetal membrane MMP activity (nor shown). FIG. 2A illustrates the gelatinolytic activity in fetal membranes in the presence or absence of LPS. Zymographically, we did not observe a significant increase in MMP concentration after LPS alone. However, NAC (10 mM) dramatically inhibited MMP-2 and MMP-9 both in the presence and absence of LPS.

Figure 3A:
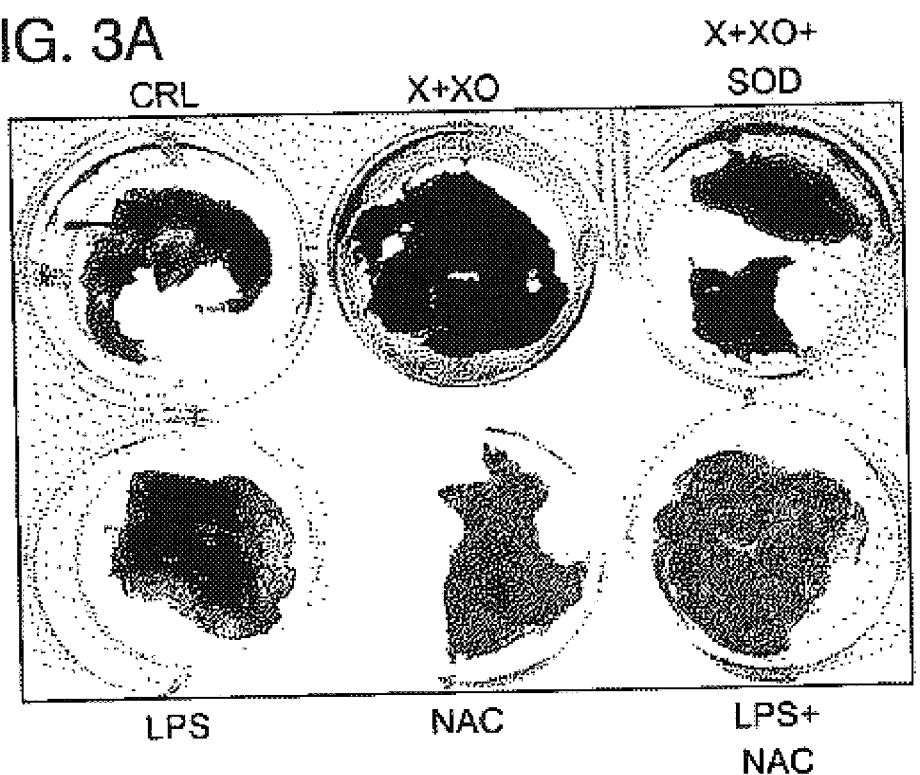
FIG. 3A illustrates the macroscopic aspect of fetal membranes incubated for 3 hours in Krebs buffer containing 1 mM nitroblue tetrazolium (CRL) and in the presence of in the presence of xanthine (X: 2 mM), xanthine and xanthine oxidase (X+XO: a source of $O2\ddot{Y}-$), X+XO with superoxide dismutase (500 U/ml), X+XO+SOD, E coli lipopolysaccharide (LPS: 100 nM), N-acetylcysteine SAC: 10 mM), LPS+NAC. The dark areas of discoloration (originally purple) of the tissue is due to the formation of intracellular or both intra and extracellular formazan precipitates (X+XO).
Figure 3B:
FIG. 3B illustrates the microscopic aspect of the fetal membranes incubated with X+XO with formazan deposits in choriodecidua. Original magnification: 300×.

Intracellular generation of $O_2^-$ in fetal membranes: When exposed to NBT over the 3 hour incubation period, there was spontaneous formation of formazan as shown macroscopically in FIG. 3A. Exposure to the X/XO reaction produced both intracellular (intense purple discoloration of the tissue which is as a darkened area in FIG. 3A) and extracellular formazan formation (discoloration of the incubation medium). The addition of SOD inhibited completely the extracellular and only partially the intracellular formazan formation. NAC (10 mM) completely abolished formazan formation in the incubated tissue. When examined by light microscopy, the deposits of formazan induced by X/XO were localized mainly within chorion laeve, decidua and amniotic epithelium. Scattered deposits were also seen in the connective tissue layer between amnion and chorion. In CRL tissues, discrete deposits were localized in the chorion, decidua as well as in large areas of the amniotic epithelium (FIG. 3B). In tissues exposed to NAC there were no formazan deposits indicating a complete inhibition of intracellular $O_2^-$ formation.

Conclusion

These experiments demonstrate that (i) MMP-9 levels in human fetal membranes are directly increased by superoxide anion, (ii) the glutathione precursor N-acetyl-cysteine (NAC) dramatically inhibits amnio-chorionic matrix metalloprotease activity in addition to inhibiting intrinsic superoxide generation within the tissue. It is, however, possible that the effect of NAC on MMP activity to extend beyond inhibition of ROS-induced effects since treatment with NAC inactivated parallel MMP-2 along with MMP-9. Moreover, the ability of NAC to inhibit MMP activity becomes more valuable as it involves total gelatinolytic activity examined by zymography (the resultant of MMP release, MMP activation and MMP/TIMP interaction).

Together, these findings suggest that the overall reduction/oxidation status of the local environment may be an important modulator of MMP levels. An increase in the oxidative state could enhance extracellular matrix degradation. Conversely, any thiol-reducing agent (NAC being just one example) could act as inhibitors of MMP activation within fetal membranes and thus may prevent premature rupture of membranes secondary to inflammation or other conditions associated with high ROS production.

b) Effect of ROS Modulation In Vivo

Materials and Methods:

Animals and treatments: C57B16 inbred mice were housed together with CD57/BL6 males under regular light and dark cycles, with stable ambient temperature conditions. The next morning the females were examined for the presence of a vaginal plug. The day of detection of the vaginal plug was designated as day 0. On day 16 of pregnancy the pregnant mice were injected i.p. with either 10 µg lipopolysaccharide (LPS: from E Coli 0111.:B4 from Calbiochem) or saline (controls). N-Acetylcysteine 1 g/kg (NAC: which is a membrane permeable GSH precursor, Sigma, St. Louis Mo. and direct antioxidant) was given p.o. by gavage 30 min before and 2 h after the LPS injection. NAC was diluted in phosphate buffered saline (PBS). After 12 hours the animals were inspected hourly for signs of parturition (posture, bleeding). The time between LPS injection and delivery of the first pup was defined as latency. Fetal viability at birth was recorded after tactile stimulation of the pup. To separate between the effect of prematurity on the fetus and the in utero consequence of endotoxin administration on the fetus, animals were sacrificed at 3, 6 and 16 hours after endotoxin injection in a separate set of experiments.

Placental extracellular superoxide production: Placental extracellular superoxide production was determined by the SOD-inhibitable reduction of nitroblue tetrazolium. Briefly, after sacrifice duplicate placentas where incubated each in 1 ml 1 mg/ml nitroblue tetrazolium (NBT) diluted in PBS, for 1 h. in a $CO_2$ incubator with humidified chamber at 37° C. The soluble yellow form of NBT is reduced by $O_2^-$ generated within the tissue to form an insoluble precipitate of blue-purple formazan that discolorates the tissue. Extracellular $O_2^-$ produces a discoloration of the incubation medium. The incubation was performed in the presence and absence of SOD. The difference in absorbance at 655 nm normalized by the dry weight of placenta between the average of the duplicates in the presence and absence of SOD represents the SOD-inhibitable $O_2^-$ production and was expressed in normalized arbitrary units.

Measurement of total glutathione: Glutathione content was measured in maternal and fetal livers of animals treated with and without NAC and sacrificed at 3, 6 and 16 hours after LPS injection. Fetal livers were pooled from all fetuses of each pregnant animal, snap frozen in liquid nitrogen and stored at −80° C. until assayed. Briefly, the frozen tissue was rapidly homogenized in 7.5% trichloroacetic acid in a ratio of 1:20 (w/v). The homogenate was centrifuged at 3000 g for 10 min at 4° C. Total glutathione content was assayed in the supernatant by a colorimetric reaction that involves the formation of a chromophoric thione (Bioxytech GSH-420, Oxis Health Products, Portland, Oreg.) and was expressed in µg/ml by using oxidized glutathione standards and further normalized by the total protein content of the pellet. The protein pellet was solubilized in 0.1 N NaOH and its protein content was estimated using a BCA protein assay kit (Pierce, Rockford, Ill.).

Figure 4A:
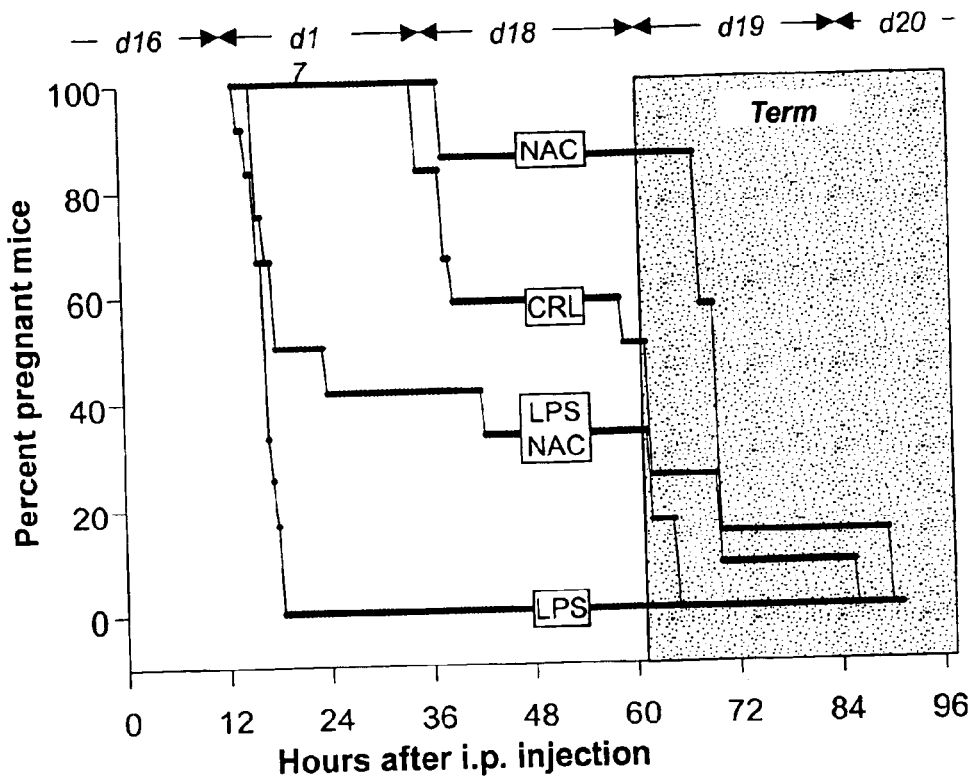
FIG. 4A is a graph showing the percent of mice that went into labor as a function of time (hours) after LPS or sham injection. C57B16 inbred mice were injected ip with 10 $\mu$mg/kg LPS. Control mice (CRL) were injected with saline. Forty-five min. before and 2 hours after the LPS or saline injection mice received po 1 mg/kg N-acetylcysteine SAC) or 0.3 ml vehicle. The numbers of animals in each group are: n=12 (CRL), n=13 (LPS), n=8 (NAC) and n=12 (LPS/NAC).
Figure 4B:
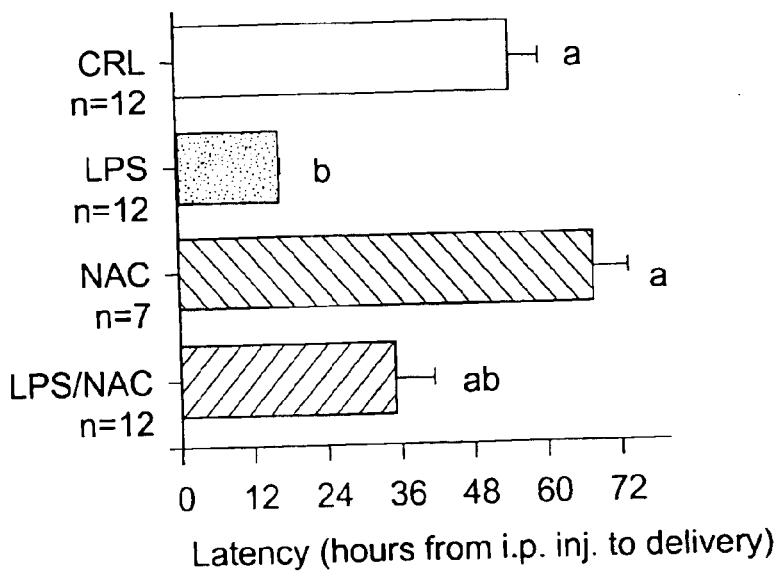
FIG. 4B is a graph showing latency (mean+SEM of the time in hours from LPS injection until delivery) in mice that were injected with endotoxin (LPS) and treated with N-acetylcysteine (LPS/NAC; n=12) or vehicle (LPS; n=12). Control mice were injected with 0.1 ml saline and given po vehicle (CRL; n=12) or N-acetylcysteine (NAC; n=7). The mean marked with asterisk is statistically different from CRL at a value of $p<0.01$ (One Way ANOVA followed by post-hoc comparisons using Student-Neuman-Keuls tests).

Results:

Effects of N-acetylcysteine on the timing of birth: Animals given two doses of 1 mg/kg NAC per os, 1 h before and 2 h after LPS, had a latency period of 35.13±6.41 h (n=12). Animals given NAC alone delivered at 67.71±5.8 h (n=7) compared to the saline injection (FIG. 4A). However, in our experiments there were also CRL animals that delivered earlier. This is consistent with observations made by other authors when using this inbred stain of mice (Swaisgood et al., 1997). Though the Kaplan-Maier survival analysis of cumulative birth rates did not reveal a significant NAC effect, the number of animals in each group was too small to exclude a type I error. However, the addition of NAC shifted latency from a statistically significant decrease with LPS alone to a value no longer different from either CRL or LPS animals (FIG. 4B).

Effects of N-acetylcysteine on fetal outcome: The mother cannibalizes the stillborn pups and covers the live born with her body. Some of the animals given NAC with LPS delivered live and stillborn pups. There were no statistically significant differences in litter sizes (number of pups/dam) among the four groups. The percent of pups born alive versus stillborn is presented in FIGS. 5A and 5B. It illustrates the statistically significant increase in the proportion of pups born alive in mice given NAC before and after LPS. To discriminate between a direct effect of LPS on the fetus and the indirect effects of prematurity, and to identify the time frame when fetal death occurred, we repeated the experiment sacrificing the animals at 3, 6 and 16 hours after LPS. No mouse delivered prematurely, or had signs of labor (vaginal bleeding) at these times. All fetuses were alive in utero at 3 and 6 h. By 16 h after LPS, 63% of the fetuses were dead in the LPS group compared to 37% in the group that received LPS plus NAC (p=0.006). These results strongly suggest that death occurs in utero and is the result of inflammation, not prematurity. Labor itself may further kill some compromised fetuses as in the LPS group since the vaginal stillbirth rate was 100%. This agrees with Sastre et al., (1994) who suggested that birth is an oxidative stress for the fetus, increasing by 11 fold hepatic GSSG in neonatal rats and that this redox alteration induced by birth per se was prevented by the maternal administration of NAC. These results suggest that NAC improves fetal outcome in a murine model of preterm birth and fetal demise induced by inflammation.

Effect of NAC on placental superoxide production: There was a 2.7 fold increase in extracellular $O_2^-$ production in placentas from LPS-injected animals at 3 hours. This increase was not seen in animals that had also received NAC. At 16 hours after LPS, placentas from all three groups produced a similar amount of formazan in the medium.

These results suggest that NAC acts as a free radical scavenger at the level of the placenta in a murine model of preterm birth and fetal demise induced by inflammation.

Figure 6A:
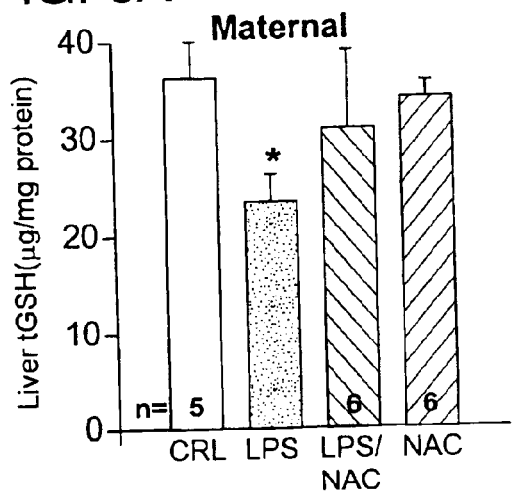
FIG. 6A is a graph showing the total glutathione content ($\mu$mg/mg protein) in the liver of mothers from animals that were treated in vivo as described herein.
Figure 6B:
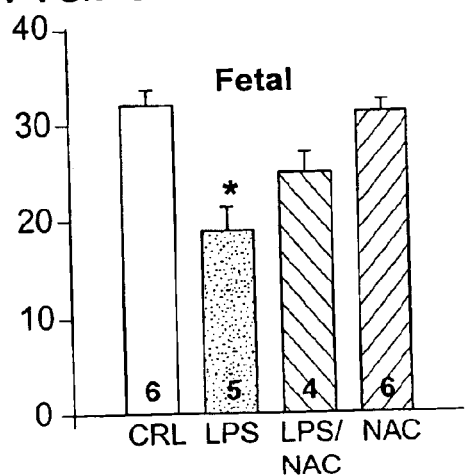
FIG. 6B is a graph showing the total glutathione content ($\mu$mg/mg protein) in the liver of fetuses from animals that were treated in vivo as described herein. Animals were sacrificed at 16 h after LPS or saline injection. The number of animals in each group is shown at the bottom of the bar. The means marked with asterisk are significantly different at a level of $p<0.05$ (maternal) or $p<0.01$ (fetal) compared to CRL levels. (One Way ANOVA followed by post-hoc comparisons using Student-Neuman-Keuls tests).
Figure 6C:
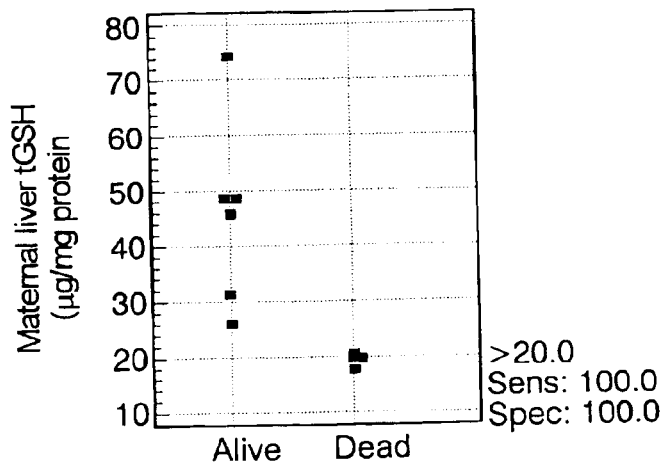
FIG. 6C is a graph showing the receiver operating curve analysis of fetal outcome (dead or alive in utero) at 16 h after LPS as a function of maternal hepatic glutathione content.

Effect of LPS and NAC supplementation on total glutathione content: Hepatic glutathione was measured to test the efficacy of p.o. NAC. There were no statistically significant differences in maternal or fetal liver GSH among groups 3 h after LPS. At 16 h (FIG. 6A), livers from pregnant mice that received LPS had significantly lower GSH compared to saline-CRL. NAC prevented the decrease in GSH of LPS-treated animals. There was, however, a high degree of variability in the NAC+LPS group. Of great potential importance, GSH content was lower in the livers of fetuses in mice injected with LPS (FIG. 6B). NAC elevated GSH content in fetal livers to values not different from either CRL or LPS. This strongly suggests that maternal treatment with NAC may have a beneficial effect on the fetal oxidative state. Co-administration of NAC prevented maternal liver glutathione depletion, though the bioavailability of NAC administered per os seems variable. We have further observed that fetal death was more likely if the maternal hepatic GSH was low (FIG. 6C). These results suggest that maternal administration of endotoxin, which results in an occult inflammatory process within the mother, induces increased glutathione consumption in the fetus. Co-administration of NAC was able to prevent maternal liver glutathione depletion during systemic inflammation.

Conclusion

NAC, a membrane permeable glutathione precursor and direct antioxidant significantly increases fetal survival in an animal model of preterm birth and fetal demise induced by inflammation. Although NAC likely delays the onset of preterm birth in this model and thus alters the duration of gestation. The protective effects of NAC on the fetus are independent of prematurity. These beneficial effects may be related to the decrease in free radical production in the placenta in response to endotoxin. In addition, adverse fetal outcome is strongly associated with an inflammatory state of the mother even in the absence of any general signs of maternal infection and inflammation. Furthermore, the inflammatory state of the mother may result in a shift in the redox balance with glutathione depletion in the fetus.

To date there are no therapeutical agents that target free radical production in the fetus either directly or transplacentally through the pregnant mother because the pathophysiological connection between free radicals, preterm birth and perinatal outcome is only now being elucidated. The findings of the present invention are unique. Glutathione or other compounds that scavenge reactive oxygen species significantly improve fetal outcome when administered in amurine model of preterm birth with intrauterine fetal demise. Although the timing of gestation with NAC was not significantly altered, NAC inhibits matrix metalloprotease activity in human fetal membranes. Activation of MMP-9 is followed by crucial catabolic processes that occur in human amniochorionic membranes during PPROM.

Free radical trapping compounds, (thiols and other chemical classes), anti-oxidants, glutathiones, and similar compounds appear to have beneficial effects for the treatment and prevention of fetal complications leading to neonatal handicaps secondary to inflammation that also causes preterm parturition. Precursors to free radical trapping compounds also have this beneficial effect. Agents that stimulate the production of endogenous free radical trapping compounds also have this beneficial effect.

It has been suggested by others that one of the mechanisms by which ROS act are as messenger molecules in mammalian cells through the activation of transcription factors such as the nuclear factor kappa beta (NFκB) or activator protein 1 (AP-1). NFκB consists of two subunits p65 and p50 and usually exists as a molecular complex with the inhibitory protein IκB in the cytosol (Baeuerle and Baltimore, 1988). Upon stimulation with proinflammatory cytokines, IκB is dissociated and NFκB is translocated to the nucleus were it activates expression of target genes. $H_2O_2$, for example, can induce early gene expression of cytokines (Los et al., 1995). Pretreatment of cells with antioxidants such as NAC efficiently inhibited both cytokine-induced NFκB activation cascade (Khachigian et al., 1997) and induction of AP-1 (Bergelson et al., 1994). In addition, both tyrosine kinase-mediated NFκB and c-Jun/AP-1 activation were proven to be essential to the induction of MMP-9 by cytokines (Yokoo and Kitamura, 1997). Thus, compounds which inhibit NFκB may have the same therapeutic effect as ROS inhibitors and are included under our claims.

The Transplacental Passage of Spin Trapping Compounds

In addition, some of the compounds described herein for detecting and scavenging FR (spin traps) have been evaluated recently in conjunction with a new non-invasive imaging technique–31 P NMR spin trapping by MRI (Fuji et al., 1999; Khramtsov et al., 1999). The present application describes evidence that in utero generation of FR is a cause of fetal damage and contribute to the development of preterm labor. We may expect to provide compounds (spin traps) that not only limit but also detect detrimental processes affecting the mother and child. A prerequisite for such a compound is the ability to trap FR in the fetus.

We have experimentally investigated the transplacental passage of spin trapping compounds. Methodology: C57B16 mice were injected ip with 4 mmols/kg POBN [a-(4-pyridyl-1-oxide-N-t-butylnitrone)] on day 16 of pregnancy. Animals were sacrificed at different times after injection, 2–5 fetuses collected and lipids extracted as described by Brackett et al., 1989. Electron paramagnetic spectra were obtained in a Varian EPR spectrometer equipped with an X-band microwave bridge with center field set at 3376 Gauss and modulation frequency at 100 Hz. The extracts were examined before and after in vitro addition of a hydroxyl radical generating Fenton mixture ($Fe^{2+}+H_2O_2$).

Figure 7A:
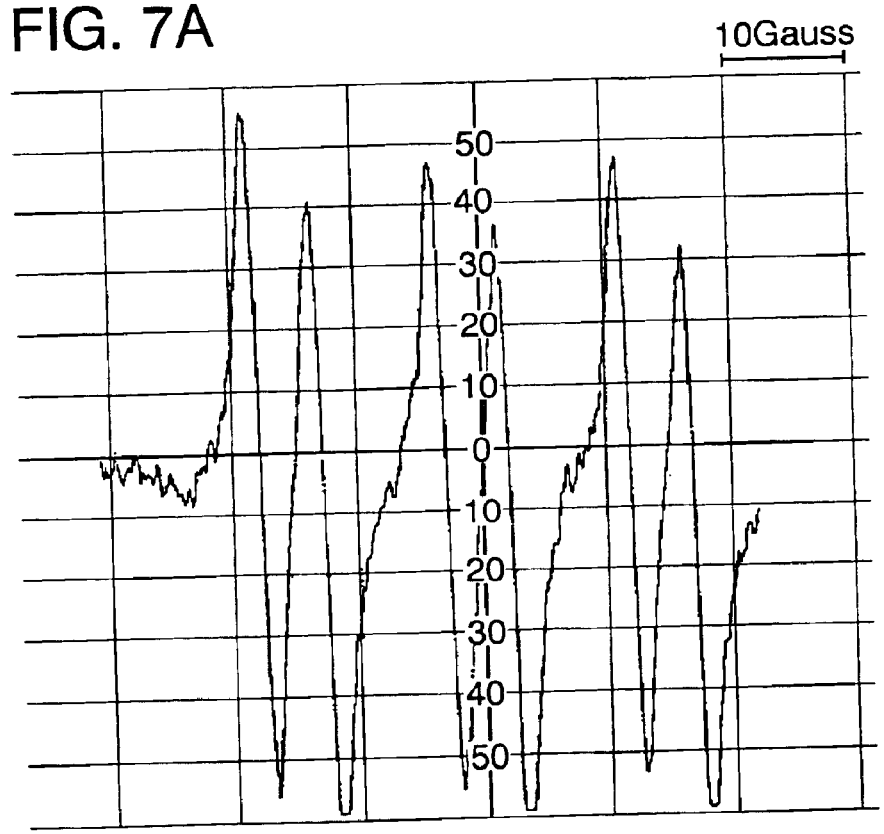
FIG. 7A is a spectrograph representing EPR spectra of the POBN-hydroxy radical spin adducts trapped in the maternal liver at 1 hour after intraperitoneal administration of POBN.
Figure 7B:
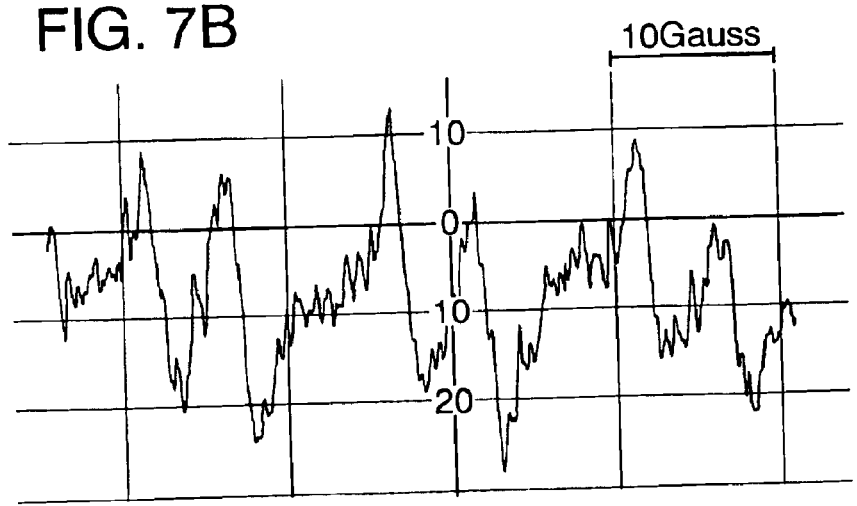
FIG. 7B is a spectrograph representing the POBN-hydroxyl radical spin adducts trapped by the amount of POBN that accumulated in the fetus within 1 hour after maternal i.p. administration of POBN.
Figure 7C:
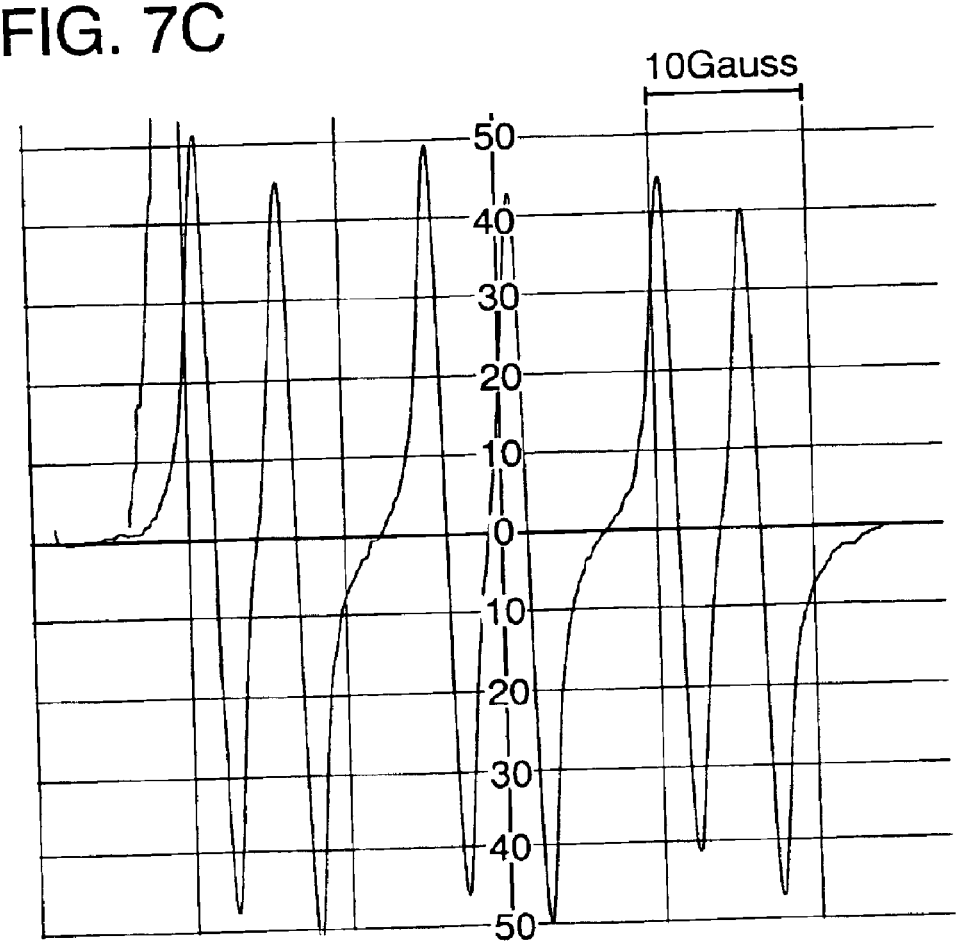
FIG. 7C is a spectrograph representing the POBN-hydroxyl radical spin adducts trapped by the amount of POBN that accumulated in the fetus within 6 hours after maternal i.p. administration of POBN.

Results: FIG. 7A represents EPR spectra of the POBN-hydroxyl radical spin adducts trapped in the maternal liver at 1 h after intraperitoneal administration of POBN. FIG. 7B and 7C illustrated the POBN-hydroxyl radical spin adducts trapped by the amount of POBN that accumulated in the fetus within 1 h or 6 h after maternal i.p. administration of POBN. There is an additional 10-fold difference in the magnitude of the signal between FIGS. 5C and A or B (Receiver gain for FIGS. 5A and B is $2\times10^5$ and for FIG. 5C is $2\times10^4$). These results indicate that FR may be trapped and detected in the fetus after maternal administration of spin trapping compounds. Transplacental passage of such compounds has not been explored before. Planned improvements include the further synthesis of specific spin traps that can be detected noninvasively by MRI imaging. Such compounds will have application not only to prevent FR damage to the fetus but also to detect in utero formation of specific FR which can induce damage to the fetus or lead to preterm labor. These findings have great clinical potential. MRI is often performed for the imaging of fetal abnormalities and is believed safe. We believe that the application of spin traps which can be administered to the mother and cross the placenta will permit in vivo quantification of FR production in both the healthy and the at risk fetus. The technology that will enable this examination already exists. Thus, treatment could be accurately initiated prior to the development of irreversible complications.

Changes may be made in the construction and the operation of various components, elements and assemblies described herein or in the steps or the sequence of steps of the methods described herein without departing from the spirit and scope of the invention as defined in the following claims.

REFERENCES

The following citations are incorporated by reference herein for details supplementing this application:

1. Athayde N, Edwin S S, Romero R, Gomez R, Maymon E, Pacora P, Menon R. A role for matrix metalloproteinase-9 in spontaneous rupture of the fetal membranes. Am J Obstet Gynecol 1998; 179: 1248–53.

2. Babior B M, Kipnes R S, Cumutte J T. Biological defense mechanisms. The production by leukocytes of superoxide, a potential bactericidal agent. J Clin Invest 1973; 52: 741–4.

3. Baeuerle P A, Baltimore D. I kappa B: a specific inhibitor of the NF-kappa B transcription factor. Science 1988; 242: 540–6.

4. Baylis C, Mitruka B, Deng A. Chronic blockade of nitric oxde synthesis in the rat produces systemic hypertention and glomerular damage. J Clin Invest 1992; 20: 278–81.

5. Beckman J S, Crow J P. Pathological implications of nitric oxide, superoxide and peroxynitrite formation. Biochem Soc Trans 1993; 21: 330–34.

6. Bergelson S, Pinkus R, Daniel V. Intracellular glutathione levels regulate Fos/Jun induction and activation of glutathione S-transferase gene expression. Cancer Res 1994; 54: 36–40.

7. Berkovitz G S, Papiemik E. Epidemiology of preterm birth. Epidemiol Rev 1993; 15: 414–3.

8. Bernstein S, Heimler R, Sasidharan P. Approaching the management of the neonatal intensive care unit graduate through history and physical assessment. [Review] Ped Clin North Am 1998; 45: 79–105.

9. Birkedal-Hansen H, Moore W G, Bodden M K, Windsor L J, Birkedal-Hansen B, DeCarlo A, Engler J A. Matrix metalloproteinases: a review. Crit Rev Oral Biol Med 1993; 4: 197–250.

10. Boelsterli U A, Lanzotti A, Goldlin C, Oertle M. Identification of cytochrome P-450-B1 as a cocaine-bioactivating isoform in rat hepatic microsomes and in cultured rat hepatocytes. Drug Metab Dispos 1992; 20: 96–101.

11. Brackett D J, Lai E K, Lemer M R, Wilson M F, McCay P B. Spin trapping of free radicals produced in vivo in heart and liver during endotoxemia. Free Radic Res Commun. 1989; 7(3–6): 315–24.

12. Buhimschi I, Ali M, Jain V, Chwalisz K, Garfield R E. Differential regulation of nitric oxide in the rat uterus and cervix during pregnancy and labor. Human Reprod 1996; 8: 101–12.

13. Buhimschi I, Yallampalli C, Chwalisz K Garfield R E. Preeclampsia-like conditions induced by nitric oxide inhibition: effects of L-arginine, D-arginine and steroid hormones. Human Reprod 1995; 10: 2723–30.

14. Buhimschi I, Yallampalli C, Dong I L, Garfield R E. Involvement of a nitric oxide-cGMP pathway in control of human uterine contractility during pregnancy. Am J Obstet Gynecol 1995; 172: 1577–84.

15. Buhimschi I A, Shi S-Q, Saade G R, Garfield R E. Marked variation in responses to chronic nitric oxide inhibition during pregnancy in outbred rats from two different colonies. Am J Obstet Gynecol (in press).

16. Chan A C, Chow C K, Chiu D. Interaction of antioxidants and their implication in genetic anemia. Proc Soc Exp Biol Med 1999; 222: 274–82.

17. Chasnoff I F, Burns W J, Schnoll S H, Burns K A. Cocaine use in pregnancy. N Engl J Med 1985; 313: 666–9.

18. Cook J L, Zaragoza D B, Sung D H, Olson D M. Expression of myometrial activation and stimulation genes in a mouse model of preterm labor: myometrial activation, stimulation, and preterm labor. Endocrinology 2000; 141: 1718–28.

19. Creasy R K. Preterm birth prevention: Where we are? Am J Obstet Gynecol 1993; 168: 1223–30.

20. DeForge L E, Fantone J C, Kenney J S, Remick D G. Oxygen radical scavengers selectively inhibit interleukin 8 production in human whole blood. J Clin Invest 1992; 90: 2123–9.

21. Diket A L, Pierce M R, Munshi U K, Voelker C A, Eloby-Childress S, Greenberg S S, Zhang X J, Clark D A, Miller M J. Nitric oxide inhibition causes intrauterine growth retardation and hind-limb disruptions in rats. Am J Obstet Gynecol 1994; 71: 1243–50.

22. Dupuy P M, Lancon J P, Francoise M, Frostell C G. Inhaled cigarette smoke selectively reverses human hypoxic vasoconstriction. Intensive Care Med 1995; 21: 941–4.

23. Eigler A, Sinha B, Hartmann G, Endres S. Taming TNF—strategies to restrain this pro inflammatory cytokine [Review] Immunol Today 1997; 18: 487–92.

24. Esteve P O, Tremblay P, Houde M, St-Pierre Y, Mandeville R. In vitro expression of MMP-2 and MMP-9 in glioma cells following exposure to inflammatory mediators. Biochim Biophys Acta 1998; 1403: 85–96.

25. Fanaroff A A, Wright I L, Stevenson D K et al., Very-low-birth-weight outcomes of the National Institute of Child Health and Human Development Neonatal Research Network, May 1991 through December 1992. Am J Obstet Gynecol 1995; 173: 1423–1431.

26. Feldman J G, Minkoff H L, McCalla S, Salwen M. A cohort study of the impact of perinatal drug use on prematurity in an inner-city population. Am J Public Health 1992; 82: 726–8.

27. Fidel P L Jr, Romero R, Cutright J, Wolf N, Gomez R, Araneda H, Ramirez M, Yoon B H. 1997 Treatment with the interleukin-I receptor antagonist and soluble tumor necrosis factor receptor Fc fusion protein does not prevent endotoxin-induced preterm parturition in mice. J Soc Gynecol Investig January-February;4(1):22–6

28. Fomin V P, Singh D M, Brown H L, Natarajan V, Hurd W W. Effect of cocaine on intracellular calcium regulation inmyometrium from pregnant women. J Soc Gynecol Investig 1999; 6: 147–52.

29. Fortunato S J, Menon R, Lombardi S J. Collagenolytic enzymes (gelatinases) and their inhibitors in human amniochorionic membrane. Am J Obstet Gynecol 1997; 177: 731–41.

30. French J F, Thomas C E, Downs T R, Ohlweiler D F, Carr A A, Dage R C. Protective effects of a cyclic nitrone antioxidant in animal models of endotoxic shock and chronic bacteremia. Circ Shock 1994; 43:130–6.

31. Fujii H, Wan X M, Zhong J H, Berliner L J, Yoshikawa K. In vivo imaging of spin-trapped nitric oxide in rats with septic shock: MRI spin trapping Magnet Reson Med 1999; 42: 235–39.

32. Gibbs R S, Eschenbach D A. Use of antibiotics to prevent preterm birth. Am J Obstet Gynecol 1997; 177: 375–80.

33. Gibbs R S, Romero R, Hillier S L, Eschenbach D A, Sweet R L. A review of premature birth and subclinical infection. Am J Obstet Gynecol 1992; 166: 1515–28.

34. Gibson X A, Shartava A, McIntyre J, Monteiro C A, Zhang Y, Shah A, Campbell N F, Goodman S R. The efficacy of reducing agents or antioxidants in blocking the formation of dense cells and irreversibly sickled cells in vitro. Blood 1998; 91: 4373–8.

35. Goldenberg M, DuBard T, Tamura S J, Zucker S J, Voss R F. Plasma matric metalloprotease-9 (MMP-9) levels as predictors of spontaneous preterm birth. Am J Obstet Gynecol 1998; 178: S189.

36. Gomez R, Romero R, Ghezzi F, Yoon B H, Mazor M, Berry S M. The fetal inflammatory syndrome. Am J Obstet Gynecol 1998; 179: 194–202.

37. Gottschall P E, Yu X, Bing B. Increased production of gelatinase B (matrix metalloproteinase-9) and interleukin-6 by activated rat microglia in culture. J Neurosci Res 1995; 42: 335–42.

38. Grigg J, Arnon S, Chase A et al. Inflammatory cells in the lungs of premature infants on the first day of life: Perinatal risk factors and origin of cells. Arch Dis Child 1993; 69: 40–43.

39. Gryglewski R J, Palmer R M, Moncada S Superoxide anion is involved in the breakdown of endothelium-derived vascular relaxing factor. Nature 1986; 320(6061): 454–6.

40. Haywood J L, Goldenberg R L, Bronstein J, Nelson K G, Carlo W A. Comparison of perceived and actual rates of survival and freedom from handicap in premature infants. Am J Obstet Gynecol 1994; 171: 432–9.

41. Henderson G I, Chen J J, Schenker S. Ethanol, oxidative stress, reactive aldehydes, and the fetus Review. Front Biosci 1999; 4:D541–50.

42. Higby K, Xanakis E M J, Pauerstein C J. Do tocolytic agents stop preterm labor? A critical and comprehensive review of efficacy and safety. Am J Obstet Gynecol 1993; 168: 1247–59.

43. Holzman C, Paneth N, Little R, Pinto-Martin J. Perinatal brain injury in premature infants born to mothers using alcohol in pregnancy. Neonatal Brain Hemorrhage Study Team. Pediatrics 1995; 95: 66–73.

44. Homandberg G A, Hui F, Wen C, Fibronectin fragment mediated cartilage chondrolysis. I. Suppression by anti-oxidants. Biochim Biophys Acta 1996; 1317:134–42.

45. Huie R E, Padmaja S. The reaction of nitric oxide with superoxide. Free Radic Res Commun 1993; 18: 195–9.

46. Iams J D (ed). Preterm labor. Clin. Obstet. Gynecol 1995; 38: 673–810.

47. Ischiropoulos H, Zhu L, Chen J, Tsai M, Martin J C, Smith C D, Beckman J S. Peroxynitrite-mediatedtyrosine nitration catalyzed by superoxide dismutase. Arch Biochem Biophys 1992; 298: 431–7.

48. Jones K L, Smith D W, Ulleland C N, Streissguth P. Pattern of malformation in offspring of chronic alcoholic mothers. Lancet 1973; 1(7815): 1267–71.

49. Junqueira L C, Zugaib M, Montes G S, Toledo O M, Krisztan R M, Shigihara K M. Morphologic and histochemical evidence for the occurrence of collagenolysis and for the role of neutrophilic polymorphonuclear leukocytes during cervical dilation. Am J Obstet Gynecol 1980; 138: 273–81.

50. Khachigian L M, Collins T, Fries J W. N-acetyl cysteine blocks mesangial VCAM-1 and NF-kappaB expression in vivo. Am J Pathol 1997; 151: 1225–9.

51. Khramtsov V, Berliner L J, Clanton T L. NMR spin trapping: Detection of free radical reactions using a phosphorus-containing nitrone spin trap. Magnet Reson Med 1999; 42: 228–34.

52. Kolas T, Nakling J, Salvesen K A. Smoking during pregnancy increases the risk of preterm births among parous women. Acta Obstet Gynecol Scand 2000; 79: 644–8.

53. Kono H, Rusyn I, Yin M, Gabele E, Yamashina S, Dikalova A, Kadiiska M B, Connor H D, Mason R P, Segal B H, Bradford B U, Holland S M, Thurman R G. NADPH oxidase-derived free radicals are key oxidants in alcohol-induced liver disease. J Clin Invest 2000; 106: 867–72.

54. Kourie J I. Interaction of reactive oxygen species with ion transport mechanisms. Am J Physiol 1998; 275: C1–24.

55. Laskowska-Klita T, Szymborski J, Chelchowska M, Czerwinska B, Chazan B. Compensatory antioxidant activity in blood of women whose pregnancy is complicated by cigarette smoking. Med Wieku Rozwoj 1999; 3: 485–94

56. Liao Q-P, Buhimschi I, Saade G, Chwalisz K Garfield R E. Regulation of vascular adaptation during pregnancy and postpartum: effects of nitric oxide inhibition and steroid hormones. Hum Reprod 1996; 11: 2777-84.

57. Little B B, Snell L M, Klein V R, Gilstrap L C. Cocaine abuse during pregnancy: maternal and fetal implications. Obstet Gynecol 1989; 73:157–60.

58. Los M, Droge W, Stricker K, Baeuerle P A, Schulze-Osthoff K. Hydrogen peroxide as a potent activator of T lymphocyte functions. Eur J Immunol 1995; 25:159–65.

59. MacMicking J, Xie Q W, Nathan C. Nitric oxide and macrophage function. [Review] Annu Rev Immunol 1997; 15: 323–50.

60. Markenson G, Martin R, Foley K, Yancey M. The use of polymerase chain reaction to detect bacteria in amniotic fluid in pregnancies complicated with preterm labor. Am J Obstet Gynecol 1997; 176: S39.

61. Markovitz J H, Lewis C E, Sanders P W, Tucker D, Warnock D G. Relationship of diastolic blood pressure with cyclic GMP excretion among young adults (the CARDIA Study): influence of a family history of hypertension. Coronary Artery Risk Development in Young Adults. J Hypertens 1997;15: 955–62.

62. McCord J M, Fridovich I Superoxide dismutase. An enzymic function for erythrocuprein (hemocuprein) J Biol Chem 1969; 244: 6049–55.

63. Mccord J M, Wong K, Stokes S H, Petrone W F, English D. Superoxide and inflammation: a mechanism for the anti-inflammatory activity of superoxide dismutase. Acta Physiol Scand (Suppl) 1980; 492: 25–30.

64. Molnar M, Süitö T, Tóth T, Hertelendy F. Prolonged blockade of nitric oxide synthesis in gravid rats produced sustained hypertension, proteinuria, trombocytopenia, and intrauterine growth retardation. Am J Obstet Gynecol 1994; 170: 1458–66.

65. Monga M, Chmielowiec S, Andres R L, Troyer L R, Parisi V M. Cocaine alters placental production of thromboxane and prostacyclin. Am J Obstet Gynecol 1994; 171: 965–9.

66. Monga M, Weisbrodt N W, Andres R L, Sanborn B M. Cocaine acutely increases rat myometrial contractile activity by mechanisms other than potentiation of adrenergic pathways. Am J Obstet Gynecol 1993a; 169:1502–6.

67. Monga M, Weisbrodt N W, Andres R L, Sanborn B M. The acute effect of cocaine exposure on pregnant human myometrial contractile activity. Am J Obstet Gynecol 1993b; 169: 782–5.

68. Moody C S, Hassan H M. Mutagenicity of oxygen free radicals Proc Natl Acad Sci USA 1982; 79: 2855–9.

69. Murphy D J, Sellers S, MacKenzie I Z et al., Case control study of antenatal and intrapartum risk factors for cerebral palsy in very preterm singleton babies. Lancet 1995; 346: 1449–54.

70. Nathan C. Nitric oxide as a secretory product of mammalian cells. FASEB J 1992; 6: 3051–64.

71. Navasumnrit P, Ward T H, Dodd N J, O'Connor P J. Ethanol-induced free radicals and hepatic DNA strand breaks are prevented in vivo by antioxidants: effects of acute and chronic ethanol exposure. Carcinogenesis 2000; 21: 93–9.

72. Osawa H. Study on the morphological changes in the placenta of rats administered nitric oxide synthase inhibitor. Nippon Sanka Fujinka Gakkai Zasshi-Acta Obstet Gynaecol Jap 1996; 48: 813–20.

73. Osmers R, Tschesche H, Rath W, Szeverenyi M, Suwer V, Wolker I, Kuhn W. Serum collagenase levels during pregnancy and parturition Eur J Obstet Gynecol Reprod Biol 1994; 53: 55–7.

74. Parry S, Strauss J F 3rd. Premature rupture of the fetal membranes. N Engl J Med 1998; 338; 663–70.

75. Peristeris P, Clark B D, Gatti S, Faggioni R, Mantovani A, Mengozzi M, Orencole S F, Sironi M, Ghezzi P. N-acetylcysteine and glutathione as inhibitors of tumor necrosis factor production. Cell Immunol 1992; 140: 390–9.

76. Pourcelot S, Faure H, Firoozi F, Ducros V, Tripier M, Hee J, Cadet J, Favier A, Urinary 8-oxo-7,8-dihydro02'-deoxyguanosine and 5-(hydroxymethyl) uracil in smokers. Free Rad Res 1999; 30: 173–80.

77. Pryor W A, Squadrito G L. The chemistry of peroxynitrite: a product from the reaction of nitric oxide with superoxide. Am J Physiol 1995; 268: L699–L722.

78. Rajagopalan S, Meng X P, Ramasamy S, Harrison D G, Galis ZS. Reactive oxygen species produced by macrophage-derived foam cells regulate the activity of vascular matrix metalloproteinases in vitro. Implications for atherosclerotic plaque stability. J Clin Invest 1996; 98:2572–9.

79. Rathakrishnan C, Tiku K, Raghavan A, Tiku M L. Release of oxygen radicals by articular chondrocytes: a study of luminol-dependent chemiluminescence and hydrogen peroxide secretion. J Bone Miner Res 1992; 7: 1139–48.

80. Romero R, Athayde N, Gomez R, Mazor B, Yoon B H, Edwin SS, Ghezzi F, Berry S M. The fetal inflammatory response syndrome is characterized by the outpouring of a potent extracellular matrix degrading enzyme into the fetal circulation. Am J Obstet Gynecol 1998; 178: S3.

81. Romero R, Avila C, Brekus C A, Mazer M. The role of systemic intrauterine infection inpretern parturition. In Uterine contractility edited by R. E. Garfield, pp.319–354. Serono Symposia 1990, Norwell, M A.

82. Romero R, Mazor M, Wu Y K, Sirtori M, Oyarzun E, Mitchell M D, Hobbins J C. Infection in the pathogenesis of preterm labor. Semin Perinatol 1988; 12: 262–79.

83. Romero R, Shamma F, Avila C, Jimenez C, Callahan R, Nores J, Mazor M, Brekus C A, Hobbins J C, Infection and labor. VI. Prevalence, microbiology, and clinical significance of intraamniotic infection in twin gestations with preterm labor. Am J Obstet Gynecol 1990; 163: 757–61.

84. Romero R, Yoon B H, Mazor M, Gomez R, Gonzalez R, Diamond M P, Baumann P, Araneda H, Kenney J S, Cotton D B. A comparative study of the diagnostic performance of amniotic fluid glucose, white blood cell count, interleukin-6, and gram stain in the detection of microbial invasion in patients with preterm premature rupture of membranes. Am J Obstet Gynecol 1993; 169: 839–51.

85. Salo A L, Randall C L, Becker H C. Effect of acute ethanol and cocaine administration on gestation days 14–17 in mice. Alcohol 1996; 13: 369–75.

86. Sastre J, Asensi M, Rodrigo F, Pallardo F V, Vento M, Vina J. Antioxidant administration to the mother prevents oxidative stress associated with birth in the neonatal rat. Life Sci 1994; 54: 2055–9.

87. Seo K, McGregor J A, French J I. Preterm birth is associated with increased risk of maternal and neonatal infection. Obstet Gynecol 1992; 79: 75–80.

88. Seoud M A, Cantwell C, Nobles G, Levy D L. Outcome of pregnancies complicated by sickle cell and sickle-C hemoglobinopathies. Am J Perinatol. 1994; 11: 187–91.

89. Shah N R, Bracken M B. A systematic review and meta-analysis of prospective studies on the association between maternal cigarette smoking and preterm delivery. Am J Obstet Gynecol 2000;182: 465–72.

90. Shartava A, Shah A K, Goodman S R. N-acetylcysteine and clotrimazole inhibit sickle erythrocyte dehydration induced by 1-chloro-2,4-dinitrobenzene. Am J Hematol 1999; 62: 19–24.

91. Sladek S M, Regenstein A C, Lykins D, Roberts J M. Nitric oxide synthase activity in pregnant rabbit uterus decreases on the last day of pregnancy. Am J Obstet Gynecol 1993; 169: 1285–91.

92. Sosenko I R. Antenatal cocaine exposure produces accelerated surfactant maturation without stimulation of antioxidant enzyme development in the late gestation rat. Pediatr Res 1993; 33: 327–31.

93. Storz G, Tartaglia R, Ames B N. Transcriptional regulator of oxidative stress-inducible genes: direct activation by oxidation. Science 1990; 248: 189–94.

94. Swaisgood C M, Zu H X, Perkins D J, Wu S, Graver C L, Zimmerman P D, Iams J D, Kniss D A. Coordinate expression of inducible nitric oxide synthase and cyclooxygenase-2 genes in uterine tissue of endotoxin-treated pregnant mice. Am J Obstet Gynecol 1997; 177: 1253–62.

95. Taube H. Mechanisms of oxidation with oxygen. J Gen Physiol 1965; 49(1 Suppl): 29–52.

96. Telfer J F, Thomson A J, Cameron I T, Greer I A, Norman J E. Expression of superoxide dismutase and xanthine oxidase in myometrium, fetal membranes and placenta during normal human pregnancy and parturition Hum Reprod 1997; 12: 2306–12.

97. Tiku M L, Liesch J B, Robertson F M. Production of hydrogen peroxide by rabbit articular chondrocytes. Enhancement by cytokines. J Immunol 1990; 145: 690–6.

98. Trachtman H, Futterweit S, Garg P, Reddy K, Singhal P C. Nitric oxide stimulates the activity of a 72-kDa neutral matrix metalloproteinase in cultured rat mesangial cells. Biochem Biophys Res Commun 1996; 218: 704–8.

99. Tsukahara H, Hiraoka M, Kobata R, Hata I, Ohshima Y, Jiang M Z, Noiri E, Mayumi M. Increased oxidative stress in rats with chronic nitric oxide depletion: measurement of urinary 8-hydroxy-2'-deoxyguanosine excretion. Redox Rep 2000; 5: 23–8.

100. Tyagi S C, Kumar S, Borders S. Reduction-oxidation (redox) state regulation of extracellular matrix metalloproteinases and tissue inhibitors in cardiac normal and transformed fibroblast cells. J Cell Biochem 1996; 61: 139–51.

101. Valenzuela M A, Cartier L, Collados L, Kettlun A M, Araya F, Concha C, Flores L, Wolf M E, Mosnaim A D Gelatinase activity of matrix metalloproteinases in the cerebrospinal fluid of various patient populations. Res Commun Mol Pathol Pharmacol 1999; 104:42–52.

102. Wakulich C A, Tepperman B L. Role of glutathione in nitric oxide-mediated injury to rat gastric mucosal cells. Eur J Pharmacol 1997; 319: 333–41.

103. Watterbeg K L, Demers L M, Scott S M et al. Chorioamnionitis and early lung inflammation in infants in whom bronchopulmonary dysplasia develops. Pediatrics 1996; 97:210–5.

104. Webster W S, Brown-Woodman P D C. Cocaine as a cause of congenital malformations of vascular origin: experimental evidence in the rat. Teratology 1990; 41: 689–97.

105. Weiner C P, Knowles R G, Moncada S. Induction of nitric oxide synthases early in pregnancy. Am J Obstet Gynecol 1994; 171: 838–43.

106. Yallampalli C, Garfield R E. Inhibition of nitric oxide synthesis in rats during pregnancy produces symptoms identical to preeclampsia. Am J Obstet Gynecol 1993; 169: 1316–20.

107. Yallampalli C, Izumi H, Byam-Smith M, Garfield R E. An L-arginine-nitric oxidecyclic guanosine monophosphate system exists in the uterus and inhibits contractility during pregnancy. Am J Obstet Gynecol 1994; 170: 175–85.

108. Yang C S, Lin N N, Liu L, Tsai P J, Kuo J S. Lowered brain glutathione by diethylmaleate decreased the glutamate release induced by cerebral ischemia in anesthetized rats. Brain Res 1995; 698: 237–40.

109. Yokoo T, Kitamura M. Dual regulation of IL-1 beta-mediated matrix metalloproteinase-9 expression in mesangial cells by NF-kappa B and AP-1. Am J Physiol 1996; 270: F123–30.

110. Yoon B H, Jun J K, Romero R, Park K H, Gomez R, Choi J H, Kim I O 1997a. Amniotic fluid inflammatory cytokines (interleukin-6, interleukin-1beta, and tumor necrosis factor-alpha), neonatal brain white matter lesions, and cerebral palsy Am J Obstet Gynecol 177:19–26.

111. Yoon B H, Romero R, Kim C J, Koo J N, Choe G, Syn H C, Chi J G 1997b. High expression of tumor necrosis factor-alpha and interleukin-6 in periventricular leukomalacia. Am J Obstet Gynecol 177:406–10.

112. Zhang H, Spapen H, Nguyen D N, Benlabed M, Buurman W A, Vincent J L. Protective effects of N-acetyl-L-cysteine in endotoxemia. Am J Physiol 1994; 266: H1746–54.

113. Zhang J, Klebanoff M A, Levine R J, Puri M, Moyer P. The puzzling association between smoking and hypertension during pregnancy. Am J Obstet Gynecol 1999; 181: 1407–13.

114. Zimmerman E F, Potturi R B, Resnick E, Fisher J E. Role of oxygen free radicals in cocaine-induced vascular disruption in mice. Teratology 1994; 49: 192–201.

What is claimed is:

1. A therapy to inhibit the occurrence of premature labor or delay delivery closer to the due date for delivery in a pregnant animal experiencing excess free radical generation, said therapy comprising:

administering to said pregnant animal a free radical scavenger or a precursor thereto selected from the group consisting of glutathione, superoxide dimutose, cataluse, glutathione peroxidase, and N-acetylcysteine, in amount effective to inhibit said occurrence or achieve said delay.

2. The therapy of claim 1 further comprising:

administering to said pregnant animal an antibacterial agent in an amount effective to inhibit infection in said pregnant animal.

3. The therapy of claim 1 further comprising: administering to said pregnant animal a tocolytic agent in an amount effective to inhibit uterine contractions in said pregnant animal.

4. A therapy to inhibit the occurrence of premature labor or delay delivery closer to the due date for delivery in a pregnant animal, said therapy comprising:

administering to said pregnant animal a free radical scavenger or a precursor thereto, in an amount effective to inhibit said occurrences or achieve said delay, said free radical scavenger is a spin trapping compound.

5. A therapy for inhibiting the occurrence of premature rupture of the membranes in a pregnant animal experiencing excess free radical generation comprising:

administering to said pregnant animal a free radical scavenger agent, or precursor thereto selected from the group consisting of glutathione, superoxide dimutose, cataluse, glutathione peroxidase, and N-acetylcysteine in an amount effective to inhibit said occurrence of premature rupture.

6. A therapy for inhibiting the occurrence of premature rupture of the membranes in a pregnant animal comprising:

administering to said pregnant animal a free radical scavenger agent, or precursor thereto, in an amount effective to inhibit said occurrences of premature rupture, said agent is a precursor of said free radical scavenger and is a spin trapping compound.

7. A therapy for delaying delivery closer to the due date for delivery of a pregnant animal experiencing excess free radical generation comprising:

administering to said pregnant animal at least one spin trapping compound or a precursor thereto in an amount effective to achieve said delay.

8. The therapy of claim 1, 5, or 7 wherein said animal is selected from the group consisting of monkeys, cows, sheep, chickens, horses, dogs, cats, and elephants.

9. The therapy of claim 1, 5, or 7 wherein said animal is mammal.

10. The therapy of claim 1, 5, or 7 wherein said animal is a reptile.

11. The therapy of claim 1, 5, or 7 wherein said animal is an amphibian.

12. The therapy of claim 1, 5, or 7 wherein said animal is human.

13. The therapy of claim 1, 5, or 7 wherein said animal is a high risk patient selected from the group consisting of patients with a history of preterm labor, patients with preterm labor, cocaine users, preeclamptic patients and patients with preterm premature rupture of membranes.

14. The therapy of claim 1, 5, or 7 wherein at least one reactive free radical scavenger is a spin trapping nitrone, spin trapping nitroxide or spin trapping salicylate.

15. The therapy of claim 14 wherein the nitrone is phenyl-butyl nitrone, or trimethoxyphenyl-butyl nitrone.

16. A method for detecting in utero formation of free radicals capable of inducing fetal damage or leading to preterm labor, the method comprising:

administering a spin trap agent passable through the placental membrane and having different magnetic resonance spectra before and after a free radical is trapped;

detecting by magnetic resonance imaging the location and amount of spin trapping agents that have interacted with a free radical;

wherein the location and amount of free radical activated spin trapping agents shows the presence and amount of free radical species.

17. A therapy to inhibit the occurrence of premature labor or delay delivery closer to the due date for delivery in a pregnant animal experiencing excess free radical generation, said therapy comprising:

administering to said pregnant animal a free radical scavenger, or a precursor thereto, in an amount effective to inhibit said occurrence or achieve said delay; and administering to said pregnant animal an antibacterial agent in an effective amount to inhibit infection in said pregnant animal.

* * * * *